United States Patent
Uchiyama et al.

(10) Patent No.: US 8,206,318 B2
(45) Date of Patent: Jun. 26, 2012

(54) BLOOD TEST APPARATUS

(75) Inventors: Motonori Uchiyama, Ehime (JP);
Masaki Fujiwara, Ehime (JP);
Toshihiro Akiyama, Ehime (JP);
Yoshinori Amano, Ehime (JP)

(73) Assignee: Panasonic Corporation, Osaka (JP)

( * ) Notice: Subject to any disclaimer, the term of this patent is extended or adjusted under 35 U.S.C. 154(b) by 555 days.

(21) Appl. No.: 12/293,626

(22) PCT Filed: Mar. 22, 2007

(86) PCT No.: PCT/JP2007/055920
§ 371 (c)(1),
(2), (4) Date: Sep. 19, 2008

(87) PCT Pub. No.: WO2007/108519
PCT Pub. Date: Sep. 27, 2007

(65) Prior Publication Data
US 2010/0234768 A1    Sep. 16, 2010

(30) Foreign Application Priority Data
Mar. 22, 2006    (JP) .................................. 2006-078425

(51) Int. Cl.
*A61B 5/00* (2006.01)
(52) U.S. Cl. ...................................................... 600/583
(58) Field of Classification Search .......... 600/573–584; 606/167, 181
See application file for complete search history.

(56) References Cited

U.S. PATENT DOCUMENTS

| | | | |
|---|---|---|---|
| 5,753,429 A | 5/1998 | Pugh | |
| 5,971,941 A * | 10/1999 | Simons et al. | 600/573 |
| 2003/0109808 A1 | 6/2003 | Takinami et al. | |
| 2006/0129065 A1 | 6/2006 | Matsumoto et al. | |
| 2008/0101431 A1 | 5/2008 | Nishida | |

FOREIGN PATENT DOCUMENTS

| | | |
|---|---|---|
| JP | 10-33507 | 2/1998 |
| JP | 10-132813 | 5/1998 |
| JP | 2002-58662 | 2/2002 |
| JP | 2003-524496 | 8/2003 |
| JP | 2003-265444 | 9/2003 |
| JP | 2004-195245 | 7/2004 |
| JP | 2004-533866 | 11/2004 |
| JP | 2005-177028 | 7/2005 |
| WO | 01/64105 | 9/2001 |
| WO | 02/069782 | 9/2002 |
| WO | 2004/054445 | 7/2004 |

OTHER PUBLICATIONS

English language Abstract of JP 2003-524496, Aug. 19, 2003.
English language Abstract of JP 2004-533866, Nov. 11, 2004.
English language Abstract of JP 2004-195245, Jul. 15, 2004.

* cited by examiner

*Primary Examiner* — Jeffrey G Hoekstra
(74) *Attorney, Agent, or Firm* — Greenblum & Bernstein P.L.C.

(57) ABSTRACT

It is intended to provide a means of easily removing a portion of blood bleeding from pierced skin, which has not been taken into a blood sensor but remained on the skin, in a blood test with the use of a blood test apparatus. By using this means, it becomes unnecessary in the blood test to separately prepare a paper sheet, etc. for wiping off. More specifically speaking, a blood test apparatus wherein a blood sensor is provided within a blood sensor unit detachable to the blood test apparatus body and the blood sensor unit has a part to be in contact with the skin in the test and an absorption means. It is favorable that the part to be in contact with the skin in the test serves as the absorption means.

16 Claims, 27 Drawing Sheets

BLOOD TEST APPARATUS

TECHNICAL FIELD

The present invention relates to a blood test apparatus for examining, for example, blood component.

BACKGROUND ART

Diabetes patients need to measure the blood sugar level regularly and administer insulin based on the blood sugar level to maintain a normal blood sugar level. To maintain this normal blood sugar level, diabetes patients need to measure the blood sugar level regularly, sample a small amount of blood from fingertips using a blood test apparatus, and measure the blood sugar level from this sampled blood.

The conventional blood test apparatus generally uses a needle as a means for puncturing skin (see Patent Document 1, for example). As shown in FIG. 1, conventional blood test apparatus 1 which uses a needle as a puncturing means, includes: housing 2 that forms a chassis; cylinder body 3 that is provided at which one side of housing 2 opens; plunger 4 that moves back and forth inside cylinder body 3; handle 5 to which one end of plunger 4 is connected; latch part 6 that latches handle 5 on housing 2; spring 7 that urges handle 5 toward opening part 3a of cylinder body 3; lancet 9 which has one end held by plunger 4 and the other end attached with blood collection needle (hereinafter "needle") 8; holding part 11 that holds blood sensor 10 on the side of opening part 3a; and electrical circuit section 12 to which the output of sensor 10 is connected. Further, a blood test apparatus with blood sensor 10 made of replaceable member is also provided.

Blood test apparatus 1 is abutted on the skin of the patient, and latching of latching part 6 is released. Then, handle 5, urged by spring 7, is propelled in the direction of arrow 14. By this release of latching of handle 5, needle 8, connected to the handle 5 via plunger 4 and lancet 9, is also propelled at the same time. Needle 8 breaks through blood sensor 10 and punctures skin 13.

A small amount of blood flows out from punctured skin 13. The outflowing blood is guided inside blood sensor 10. The blood guided into blood sensor 10 causes chemical changes in blood sensor 10 according to the blood sugar level of the patient. The current produced by the chemical changes is led to electrical circuit section 12, and the blood sugar level is measured. The calculated blood sugar level is displayed on display section 15. Based on the calculated blood sugar level, for example, basic data showing the amount of insulin to administer to the patient is provided.

On the other hand, an apparatus for sampling blood using laser light for the puncturing means, is also proposed (see Patent Documents 2 and 3). Use of laser light provides an advantage of making unnecessary replacement of the needle and possibly alleviating the pain of the patient upon puncturing.

Patent Document 1: Japanese Patent Application Publication No. 2003-524496
Patent Document 2: Japanese Patent Application Publication No. 2004-533866
Patent Document 3: Japanese Patent Application Laid-Open No. 2004-195245

DISCLOSURE OF INVENTION

Problems to be Solved by the Invention

Even if a blood test apparatus uses any puncturing means, cases occur where part of blood flowing out from the punctured skin cannot be guided in a blood sensor and remains on the skin. Therefore, it is necessary to prepare wiping paper and wipe off the blood remaining on the skin every time blood test is carried out with the blood test apparatus. It is therefore an object of the present invention to make preparing tool to wipe off the blood after test, unnecessary.

Means for Solving the Problem

The blood test apparatus of the present invention has a blood sensor unit that can be attached to and removed from an apparatus body and that includes a blood sensor, and the blood sensor unit has an absorbing means.

Advantageous Effect of the Invention

According to the blood test apparatus of the present invention, an absorbing means is attached to the blood sensor unit including the blood sensor, so that, even if extra blood flows out by puncturing and remains on punctured skin, the absorbing means attached to the blood sensor unit can wipe off the blood. Therefore, it is not necessary to prepare tool for wiping off blood after measurement. Further, the wiped-off blood can be discarded together with the blood sensor unit, and so the blood test apparatus is sanitary.

BRIEF DESCRIPTION OF DRAWINGS

FIG. 11 shows an exploded plan view of the blood sensor, where

FIG. 30 shows a tip part of the blood sensor unit where an accordion-shaped extensible member is provided in the tip part of the holder, where

BEST MODE FOR CARRYING OUT THE INVENTION

The blood test apparatus of the present invention has: an apparatus body that has an opening part; a blood sensor held at the opening part; a puncturing means that is provided inside the apparatus body and that punctures skin; an electrical circuit section that is connected to the blood sensor; and a power supply section that supplies power to the electrical circuit section. The puncturing means may be either a needle or laser light. The blood sensor is one member of the blood sensor unit that can be attached to and removed from the apparatus body. The blood sensor unit has a part that contacts with the skin to be punctured. Preferably, the blood sensor unit contacts with the skin and thereby the internal space of the blood sensor unit is sealed.

Further, the blood test apparatus of the present invention has a negative pressure means. As described above, the internal space of the blood sensor unit is sealed by the skin to be punctured, so that the negative pressure means can create a negative pressure inside the blood sensor unit sealed by the skin. By creating a negative pressure, the skin to be punctured may be sucked in.

Overview of the Blood Test Apparatus that Performs Puncturing with a Needle

Figure 1:
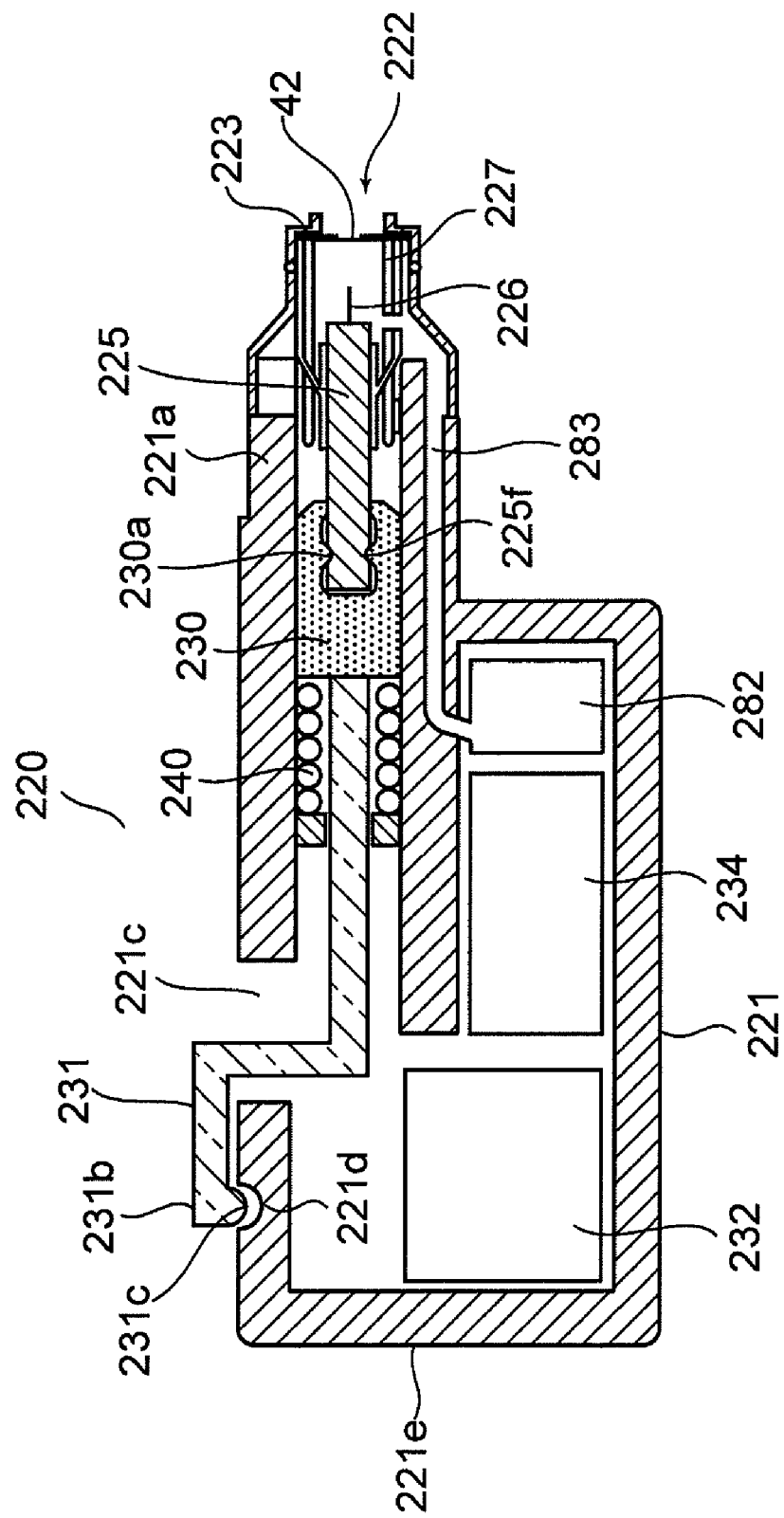
FIG. 1 is a cross-sectional view showing one example of the blood test apparatus using a needle for the puncturing means.

The blood test apparatus of the present invention may use a needle as the puncturing means. One example of the apparatus that has a needle as the puncturing means is shown in FIG. 1. FIG. 1 is a cross-sectional view of blood test apparatus 220. Blood test apparatus 220 has housing 221 formed with resin. Housing 221 is a frame of the apparatus and accommodates primary members of the apparatus. Housing 221 accommodates electrical circuit 232. Electrical circuit 232 receives a detection signal of blood components detected in blood sensor 42 (described later) and measures the blood components.

One side (upper right in the figure) of housing 221 is attaching part 221a. Blood sensor unit 222 is inserted from an end of attaching part 221a. As described later in detail, blood sensor unit 222 has: holder 223; blood sensor 42 attached inside holder 223; lancet 225 that can slide inside holder 223 freely; and blood collection needle 226 that is attached to an end part of lancet 225. Blood sensor 42 includes detection electrodes and connection electrodes connected to the detection electrodes (described later). Connector 227 contacts with the connection electrodes.

Grip part 225f formed near one end of lancet 225 which is one member of blood sensor unit 222, is held by holding part 230a provided at one end of plunger 230 that slides inside attaching part 221a. Holding part 230a of plunger 230 holds grip part 225f of lancet 225, so that, when the skin is punctured with blood collection needle 226, blood collection needle 226 does not wobble and enables high linearity of movement, so that it is possible to puncture the skin with blood collection needle 226 stably.

Plunger 230 is connected to handle 231 formed in the shape of a crank. Latch convex part 231c is formed at one end 231b of handle 231. Handle 231 goes through hole 221c formed in housing 221, and is latched by the joint of latch convex part 231c and latch concave part 221d. When the latching is released, plunger 230 urged by spring 240 pushes out lancet 225 connected with puncturing needle 226.

Housing 221 accommodates power supply section 234 that supplies power to electrical circuit 232. Further, housing 221 accommodates negative pressure means 282, and negative pressure means 282 can create a negative pressure inside blood sensor unit 222 via negative pressure path 283.

Overview of the Blood Test Apparatus that Performs Puncturing with Laser Light

Figure 2:
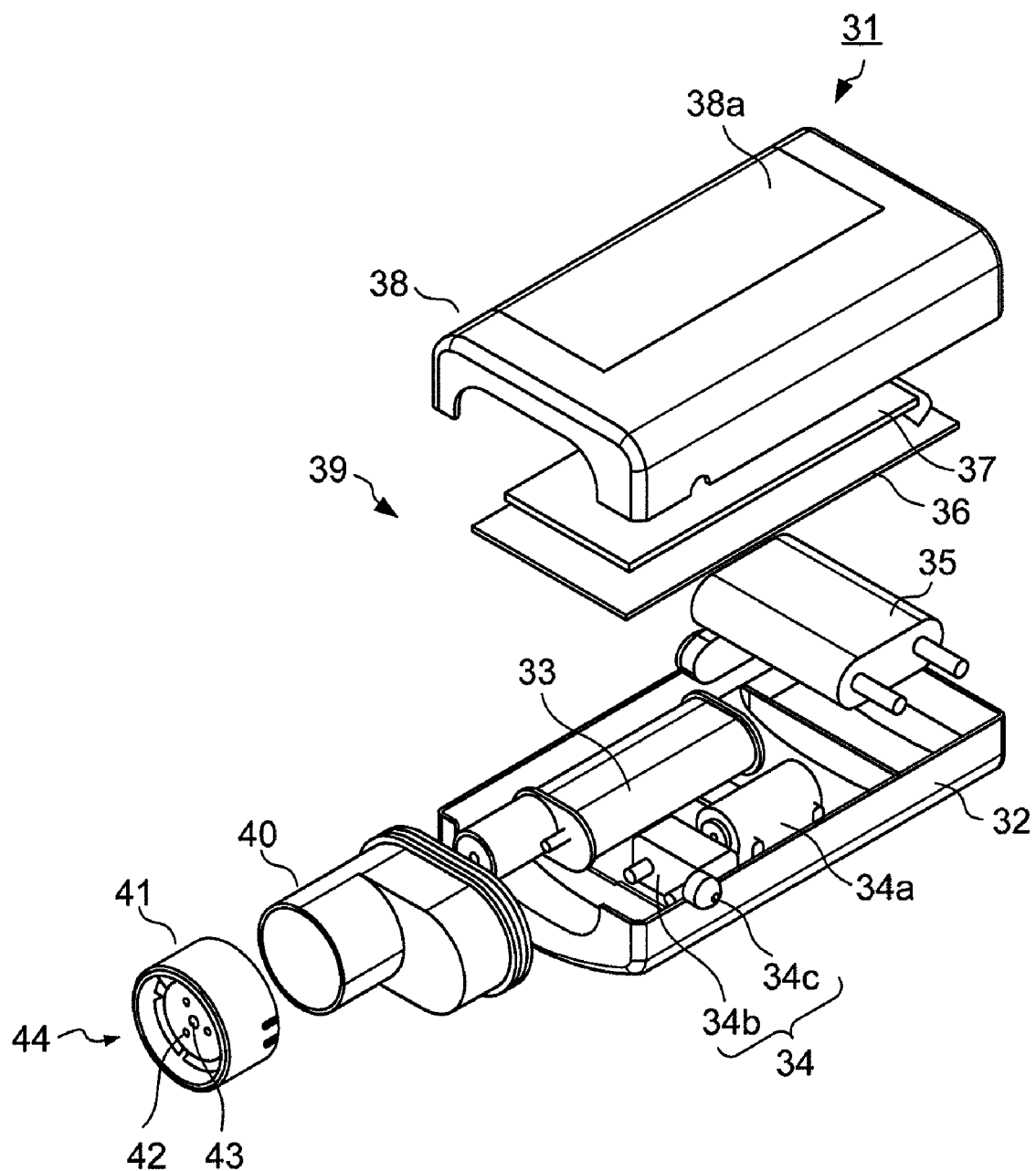
FIG. 2 is an assembly view showing one example of the blood test apparatus using laser light for the puncturing means.

The blood test apparatus of the present invention may use laser light as the puncturing means. An example of the apparatus that uses laser light as the puncturing means is shown in FIG. 2 (assembly perspective view). The interior of lower case 32 of blood test apparatus 31 shown in FIG. 2 accommodates components including: laser emitting apparatus 33; negative pressure means 34 which is configured with suction pump 34a, pump valve unit 34b and vent switch 34c; battery 35 which supplies power to electrical components; electrical circuit section 36 which is mounted on these components; and display section 37 which is mounted on electrical circuit section 36, and, for example, made of liquid crystal. Apparatus body 39 is configured so that upper case 38 covers lower case that accommodates the components. Transparent display window 38a is provided in upper case 38 in the position corresponding to display section 37.

Apparatus body 39 is connected to blood sensor unit 44 via adapter 40. One end of adapter 40 is a cylinder-shaped body, and blood sensor unit 44 is inserted removably into adapter 40. Blood sensor unit 44 is configured with holder 41 and blood sensor 42 attached inside holder 41. Window 43 provided in the center of blood sensor unit 44 is apart allowing laser light from the laser emitting port of laser emitting apparatus 33 to passthrough. Window 43 maybe a hole or a member formed with a member that allows laser light to pass through.

As described above, the blood test apparatus may accommodate a laser emitting apparatus as a means for puncturing skin. When the skin is irradiated with laser light, the laser light is absorbed in the OH group of water (water in blood) on the skin, heat increases instantaneously and the water evaporates. By the increase of the temperature, the water evaporates and pushes up the skin. The pushed-up skin is destroyed (a hole is opened) and blood flows out. After blood 16 flows out, the skin surface punctured with laser light is carbonized, and produces a carbonized odor. This carbonized odor may be deodorized with a deodorizer.

Figure 3:
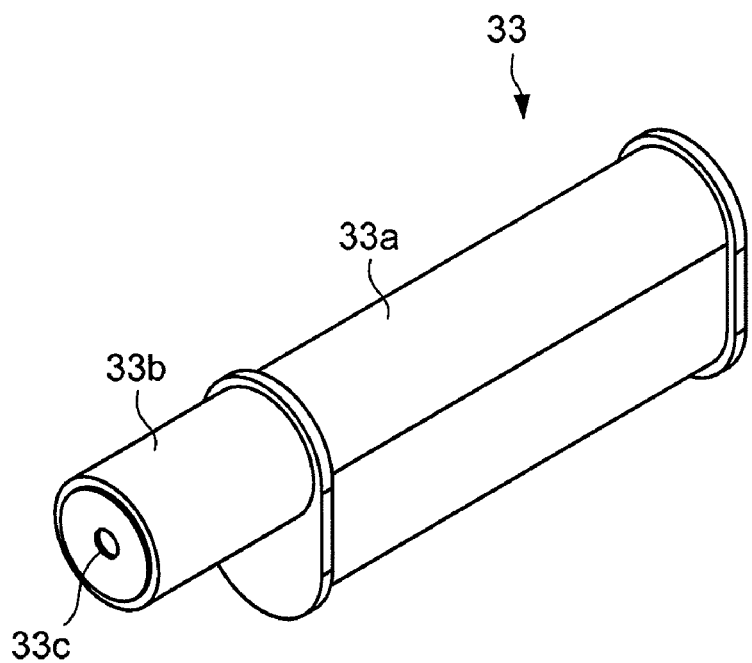
FIG. 3 is a diagrammatic perspective view of the laser emitting apparatus.
Figure 4:
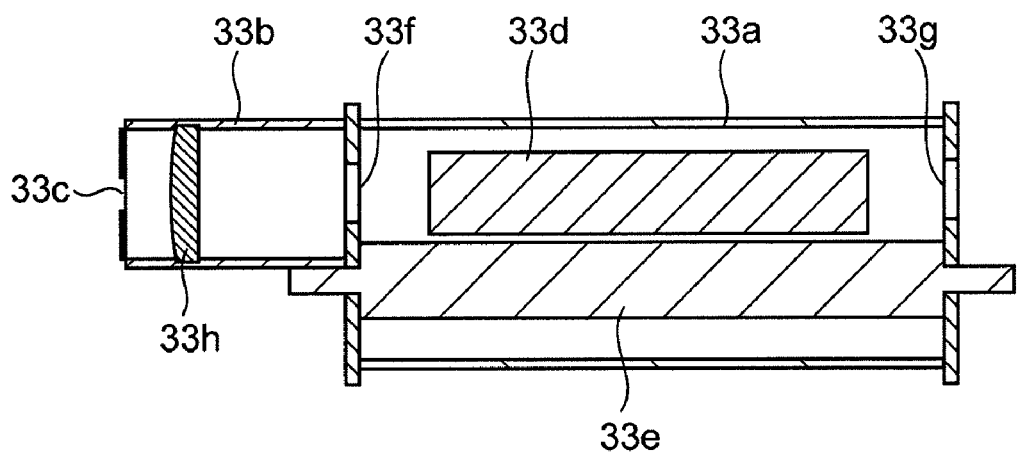
FIG. 4 is a cross-sectional view of the laser emitting apparatus.

FIG. 3 is an exterior perspective view of laser emitting apparatus 33 accommodated in the blood test apparatus. Further, FIG. 4 is a cross-sectional view of laser emitting apparatus 33. Laser emitting apparatus 33 is configured with oscillation tube 33a and cylindrical body 33b connected ahead of oscillation tube 33a. Laser emitting port 33c is provided at the center of the front edge of cylindrical body 33b.

Oscillation tube 33a accommodates inside laser crystal (for example, Er:YAG (yttrium aluminum garnet)) 33d and excitation light source 33e. Partially reflecting mirror 33f is attached in one end of oscillation tube 33a. The transmittance of partially reflecting mirror 33f may be approximately 1%. Totally reflecting mirror 33g is attached in the other end of oscillation tube 33a. Convex lens (focus lens) 33h is mounted inside cylindrical body 33b. Convex lens 33h focuses laser lights near the surface of the blood sensor. Totally reflecting mirror 33g, YAG laser crystal 33d, partially reflecting mirror 33f, lens 33h and laser emitting port 33c are arranged in this order.

To be more specific, the kind of the laser light by laser emitting apparatus 33 is Er:YAG or $CO_2$ gas, the wavelength range is 2.7 to 3.5 μm or 6.5 to 10.5 μm, the pulse width is 50 to 400 μs, preferably 200 μs, and the output is 300 mJ to 3000 mJ. The diameter of the shot is approximately 0.1 to 0.5 mm, and the depth of the shot is 0.3 to 0.7 mm. Further, the charge voltage falls in a range of 200 to 700 V, preferably 500 V. This high voltage may be obtained by charging electrical charge in a capacitor using a battery and discharging the electrical charge at a burst.

The process of emitting laser light from laser emitting apparatus 33 will be described. The excitation light emitted from excitation light source 33e penetrates inside laser crystal 33d, resonates and is amplified through laser crystal 33d reflecting between totally reflecting mirror 33g and partially reflecting mirror 33f. Part of the amplified laser light passes through partially reflecting mirror 33f by stimulated emission. The laser light passing through partially reflecting mirror 33f passes through lens 33h and is emitted from laser emitting port 33c. As described later, the laser light emitted from laser emitting port 33c punctures (illuminates) the skin.

The Blood Sensor

The blood test apparatus of the present invention has a blood sensor for taking in blood flowing out from the punctured skin and examining the blood components. The blood sensor is arranged inside the blood sensor unit.

Figure 5:
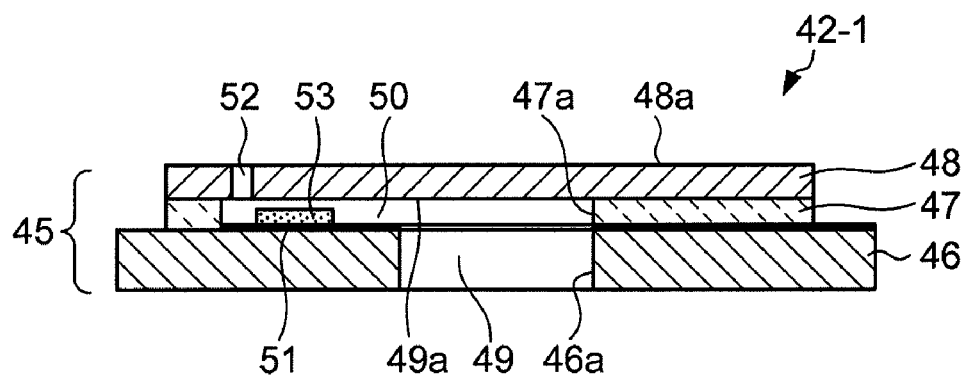
FIG. 5 is a cross-sectional view of a first example of the blood sensor.

FIG. 5 is a cross-sectional view of a first example of the blood sensor. Blood sensor 42-1 shown in FIG. S has an outer shape of a round. Base plate 45 constituting blood sensor 42 has: substrate 46; spacer 47 stacked on the upper face of substrate 46; and cover 48 stacked on the upper face of spacer 47.

Blood storing part 49 is provided near the center of base plate 45. Storing part 49 is formed to communicate with hole 46a provided in substrate 46 and hole 47a provided in spacer 47. Storing part 49 opens downward (on the side where the skin is placed) to collect blood from the skin. The volume of storing part 49 is, for example, 0.904 μL, but is by no means particularly limited. One end of supply channel 50 is connected to storing part 49. The volume of supply channel 50 is, for example, 0.144 μL, but is by no means particularly limited. Detecting section 51 is arranged inside supply channel 50.

Blood stored in storing part 49 intrudes into supply channel 50 by capillary action and is led to detecting section 51. The other end of supply channel 50 is connected to air hole 52. The diameter of air hole 52 may be approximately 50 μm. By making the diameter of air hole 52 small, blood is prevented from overflowing through air hole 52. Further, when the negative pressure means creates a negative pressure inside the blood sensor unit, a negative pressure is created inside storing part 49 via air hole 52 in a state where the skin is in close contact.

Reagent 53 mounted on detecting section 51 may be prepared as appropriate according to a test target. For example, reagent 53 is prepared by dropping a reagent solution on a detecting section arranged on substrate 46 and drying the reagent solution, wherein the reagent solution can be prepared by adding and dissolving an enzyme (PQQ-GDH) of 0.1 to 5.0 U/sensor, potassium ferricyanide (10 to 200 mM), maltitol (1 to 50 mM) and taurine (20 to 200 mM) to a 0.01 to 2.9 wt % aqueous solution of CMC.

Storing part 49 of blood sensor 42-1 is sealed with face 49a (hereinafter "ceiling face"). Therefore, when a needle is used as the puncturing means, cover 48 may be perforated with the needle to puncture the skin.

On the other hand, in the case where laser light is used as the puncturing means, it is preferable that emitted laser light can transmit through ceiling face 49a, because, because the blood flowing out from the skin punctured with laser light does not flow out from ceiling face 49a. To allow laser light to transmit through ceiling face 49a, cover 48 may be formed with a material that allows laser light to transmit (for example, glass or plastic such as polyimide). If emitted laser light cannot transmit through ceiling face 49a, the laser light may perforate ceiling face 49a.

If a needle or laser light perforates ceiling face 49a, substrate 46, spacer 47 and cover 48 can be formed with the same material, which is preferable in terms of material control and cost.

If a negative pressure means is provided in the blood test apparatus and creates a negative pressure inside the blood sensor unit, a hole formed in ceiling face 49a by a needle or laser light, together with air hole 52, becomes a negative pressure path through which the negative pressure means creates a negative pressure in storing part 49.

Figure 6:
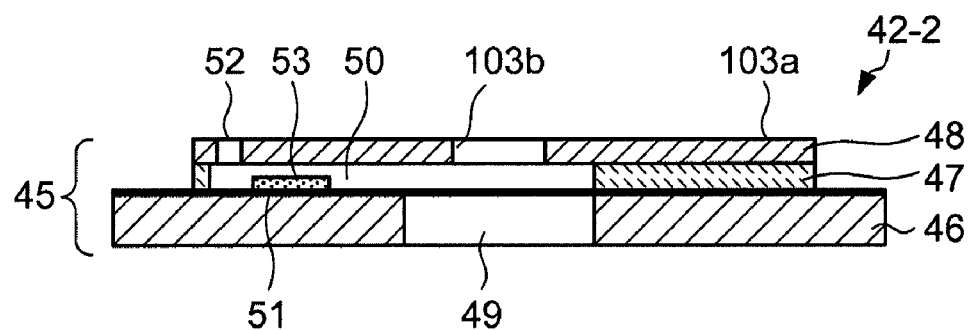
FIG. 6 is a cross-sectional view of the second example of the blood sensor.

FIG. 6 is a cross-sectional view of the second example of the blood sensor. While ceiling face 49a of storing part 49 of blood sensor 42-1 shown in FIG. 5 is sealed, the ceiling face of storing part 49 of blood sensor 42-2 shown in FIG. 6 is open.

Hole 103b is formed in cover 48 of blood sensor 42-2. Preferably, the diameter of hole 103b (for example, 1.0 mm) is smaller than the diameter of storing part 49 (for example, 2.0 mm), and is greater than the diameter of air hole 52 (for example, 50 μm). Hole 103b is preferably located in the center of the ceiling face of storing part 49. The needle or laser light of the puncturing means passes through hole 103b and punctures the skin. By providing hole 103b, the needle or laser light does not need to perforate the ceiling face, so that it is possible to minimize reduction of the transfer energy of the needle and attenuation of the laser light. Therefore, it is possible to reduce the force for propelling a needle or the energy of laser light to be emitted.

If a negative pressure means is provided in the blood test apparatus and creates a negative pressure inside the blood sensor unit, hole 103b, together with air hole 52, can be a negative pressure path through which the negative pressure means creates a negative pressure in storing part 49.

Figure 7:
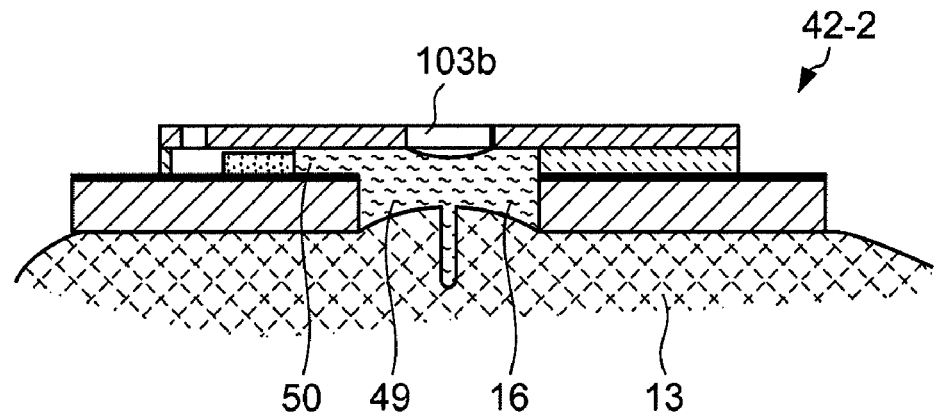
FIG. 7 illustrates a state where blood is stored in the blood sensor shown in FIG. 6.

As shown in FIG. 7, the surface tension of blood 16 inside hole 103b prevents blood 16 collected by puncturing the skin from flowing out to the upper face of the cover. Blood 16 spreads inside storing part 49, so that an adequate amount of blood 16 can be collected. Blood 16 that fills storing part 49 flows into supply channel 50.

If hole 103b is water-repellent, blood 16 is less likely to overflow through hole 103b. Therefore, the interior of blood test apparatus 31 is not contaminated with blood.

Polyethylene terephthalate (PET) can be used as the material of cover 48 of blood sensor 42-2, and the same material as substrate 46 and spacer 47 can be used. Therefore, material control is simple.

Although laser light of the puncturing means passes through hole 103b of storing part 49, laser light may pass through the center of hole 103b or pass through a position off the center of hole 103b. For example, by making laser light pass through a position further from supply channel 50 than the center of hole 103b, blood 16 flowing out from skin 13 fills the interior of storing part 49 completely, and then flows into supply channel 50, so that it is possible to realize accurate measurement.

Hole 103b is formed in advance of the puncturing in the ceiling face of the storing part of blood sensor 42-2. Hole 103b is formed in advance, so that it is not necessary to adjust the axis of the laser light to the part to be perforated. Therefore, the blood sensor is easily attached to blood sensor unit 44. The out-flowing blood 16 through the puncturing hole is preferably prevented by making the diameter of hole 103b small, approximately 0.05 to 0.2 mm.

As shown in FIG. 5 and FIG. 6, blood sensor 42 of the present invention preferably has a storing part and a supply channel. The inner wall surface of the supply channel is preferably hydrophilic, so that blood is sent smoothly to the supply channel where a detecting section is arranged. Further, the inner wall surface of the supply channel is preferably more hydrophilic than the inner wall surface of the storing part, so that blood stored in the storing part is supplied to the supply channel smoothly.

Further, as shown in FIG. 5 and FIG. 6, blood sensor 42 of the present invention has cover 48, and the cover forms the ceiling face of the storing part. Upper face 48a or 103a (faces irradiated with laser light) of the cover is preferably water-repellent. Further, the upper face of the cover is preferably more water-repellent than the inner wall surface of the storing part, so that blood stored in the storing part is prevented from flowing out through a hole formed in the cover.

Transparent Plan View 1 of the Blood Sensor

Figure 8:
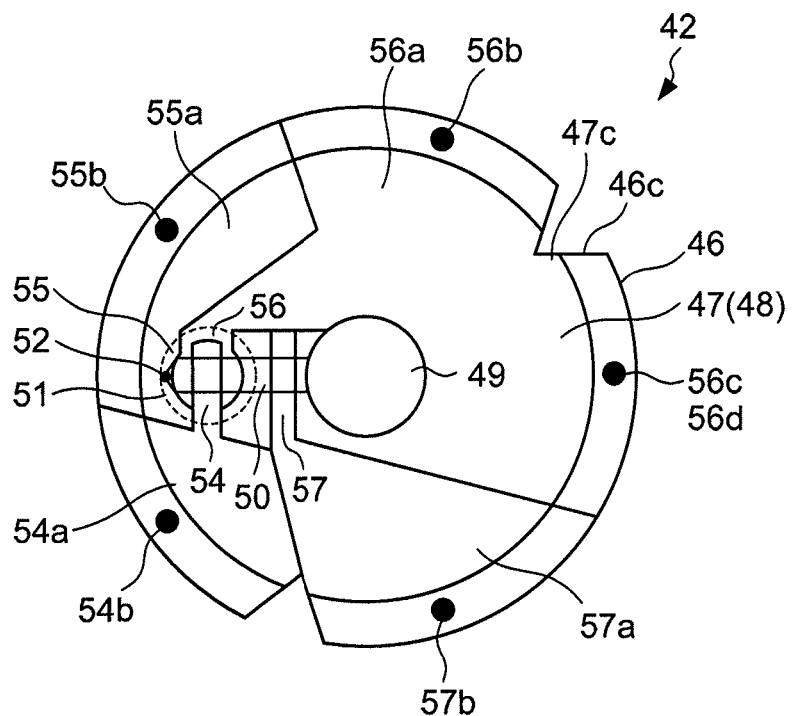
FIG. 8 is a transparent plan view of the blood sensor.

FIG. 8 is a transparent plan view of blood sensor 42. In blood sensor 42, detection electrodes 54 to 57 are arranged, and in order from storing part 49 toward air hole 52, detection electrode 57 (Hct (hematocrit) measuring electrode), detection electrode 56 (counter electrode), detection electrode 54 (active electrode), detection electrode 56 (counter electrode) and detection electrode 55 (sensing electrode) are arranged. Detection electrodes 54 to 56 are arranged on detecting section 51.

Detection electrodes 54 to 57 are connected to connection electrodes 54a to 57a, respectively. Connection electrodes 54a to 57a extend up to the outer periphery of substrate 46. Connection electrodes 54a to 57a are provided in contact parts 54b to 57b, respectively. Further, in connection electrode 56a, contact part 56c is also provided in addition to contact part 56b, that is, two contact parts are formed. Reference electrode 56d may be provided in the connection electrode (54a, 55a or 57a) other than connection electrode 56a. Contact parts 54b to 57b and contact part 56c are arranged near the outer periphery of blood sensor 42 at virtually regular intervals.

Figure 36:
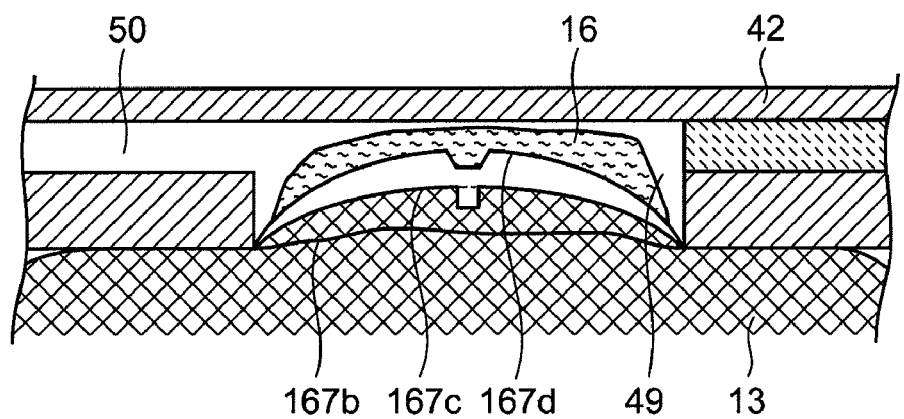
FIG. 36 shows a state where a negative pressure is created a plurality of times intermittently in a blood test using the blood test apparatus.
Figure 37:
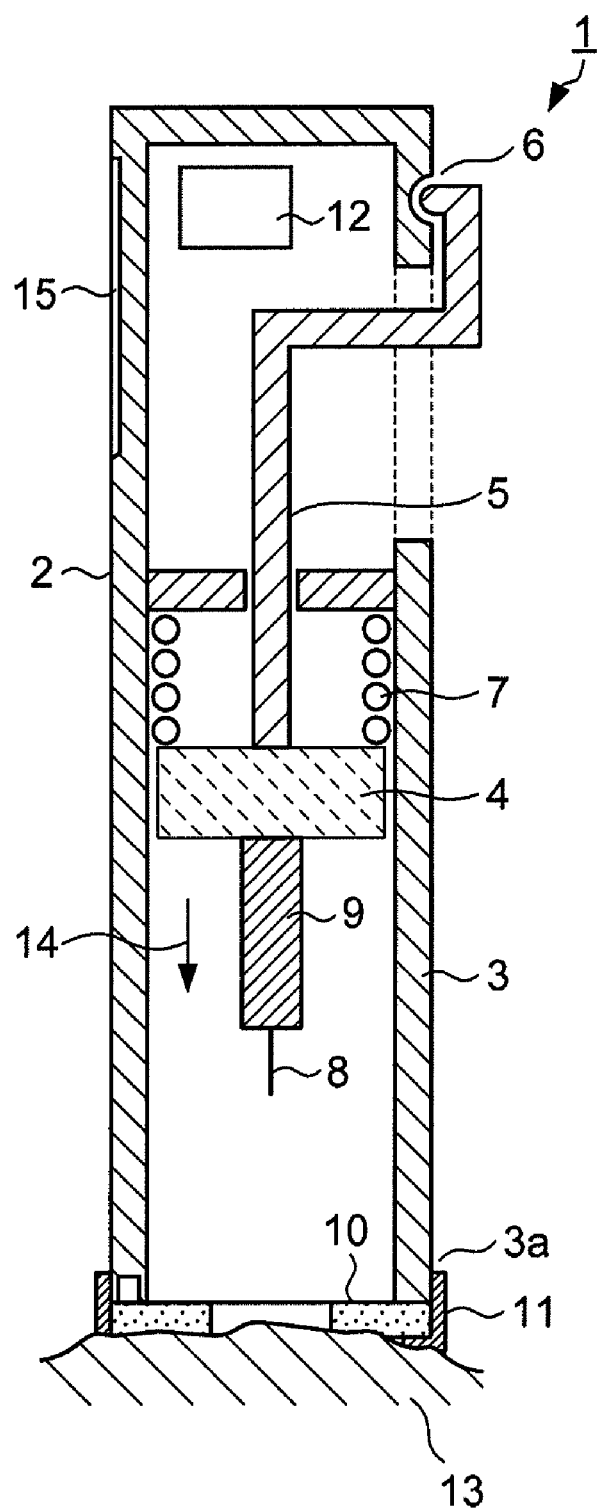
FIG. 37 is a cross-sectional view of the conventional blood test apparatus.

Out of the contact parts, contact part 56b and contact part 56c conduct with each other, and the other contact parts are insulated from each other. The connection electrodes can be specified using contact part 56c as a reference contact part, that is, reference electrode 56d. That is, the insulation resistance between the neighboring contact parts is measured by an electrical circuit section (see 232 in FIG. 1 and 36 in FIG. 2), and a contact part where the insulation resistance is zero is identified as reference electrode 56d. Based on reference electrode 56d, connection electrodes 56a, 57a, 54a and 55a are specified clockwise.

In this way, blood sensor 42 has reference electrode 56d, so that it is possible to specify the connection electrodes. Therefore, even if the contact parts (54b to 57b and 56c) are connected randomly to the five connectors arranged in the apparatus body, it is possible to specify the connection electrodes and perform measurement. Accordingly, blood sensor 42 (or a blood sensor unit including blood sensor 42) can be made a symmetrical shape so that blood sensor 42 can be attached to the apparatus body casually in a very simple manner.

Aligning concave part 46c may be provided on the outer periphery of substrate 46. Also on the outer peripheries of spacer 47 and cover 48, aligning concave parts 47c and 48c are provided so as to correspond to positioning concave part 46c. Aligning concave parts 46c to 48c become a reference for adjusting blood sensor 42 in a predetermined position of blood sensor unit 44.

Transparent Plan View 2 of the Blood Sensor

Figure 9:
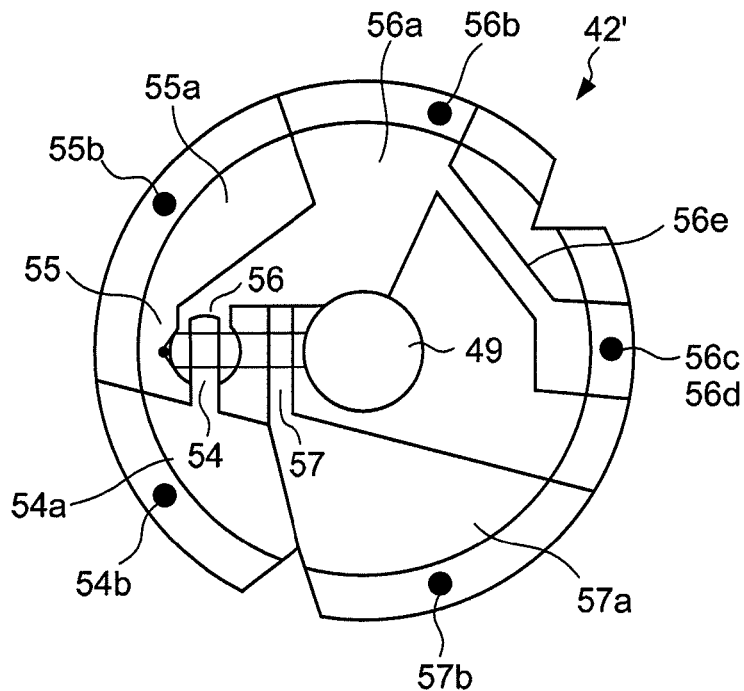
FIG. 9 is a transparent plan view of the blood sensor.

FIG. 9 is a transparent plan view of another example of round blood sensor 42'. Blood sensor 42' is different from blood sensor 42 (see FIG. 9) in that reference electrode 56d is formed via a predetermined pattern from connection electrode 56a. The difference will be mainly described below.

Reference contact part 56c is provided in reference electrode 56d. Reference contact part 56c and contact parts 54b to 57b are arranged near the outer periphery at regular intervals. That is, contact parts 54b, 55b, 56b, 56c and 57b are arranged at apex of a regular pentagon.

Connection electrode 56a and reference electrode 56d are connected via pattern 56e formed through laser-processing. By changing the width of pattern 56e, the resistance value between contact part 56b and reference contact part 56c can be changed. Reference electrode 56d serves as a reference for specifying connection electrodes 54a to 57a.

Reference electrode 56d can be utilized to identify the product specifications of blood sensor 42'. For example, the blood test apparatus is set so that calibration curve 1 is used when the resistance value of pattern 56e is 200 to 1000 ohms, calibration curve 2 is used when the resistance value is 1000 to 2000 ohms, and calibration curve 3 is used when the resistance value is 2000 to 3000 ohms, the calibration curve of the blood sensor is recognized automatically, and the blood sugar level is measured using an appropriate calibration curve. Other than the automatic recognition of the calibration curve, the reference electrode can be used to identify a product specification. For example, the reference electrode can be used to identify users the product is shipped to, for example, to identify whether the product has the specifications for company A or the specifications for company B.

By forming pattern 56e with an inductance having arbitrary property, connecting the inductance to a resonator constituting an oscillator and changing the oscillation frequency according to the inductance property. In the result, various information is provided.

By providing reference electrode 56d, even when blood sensor unit 44 is attached to blood test apparatus 31 at an arbitrary rotation angle with respect to the axis of the attaching direction, connection electrodes 54a to 57a can be specified. Therefore, when blood sensor unit 44 is attached, the attaching direction does not have to be adjusted with visual checking, so that it is possible to attach blood sensor unit 44 in a simple manner.

Transparent Plan View 3 of the Blood Sensor

Figure 10:
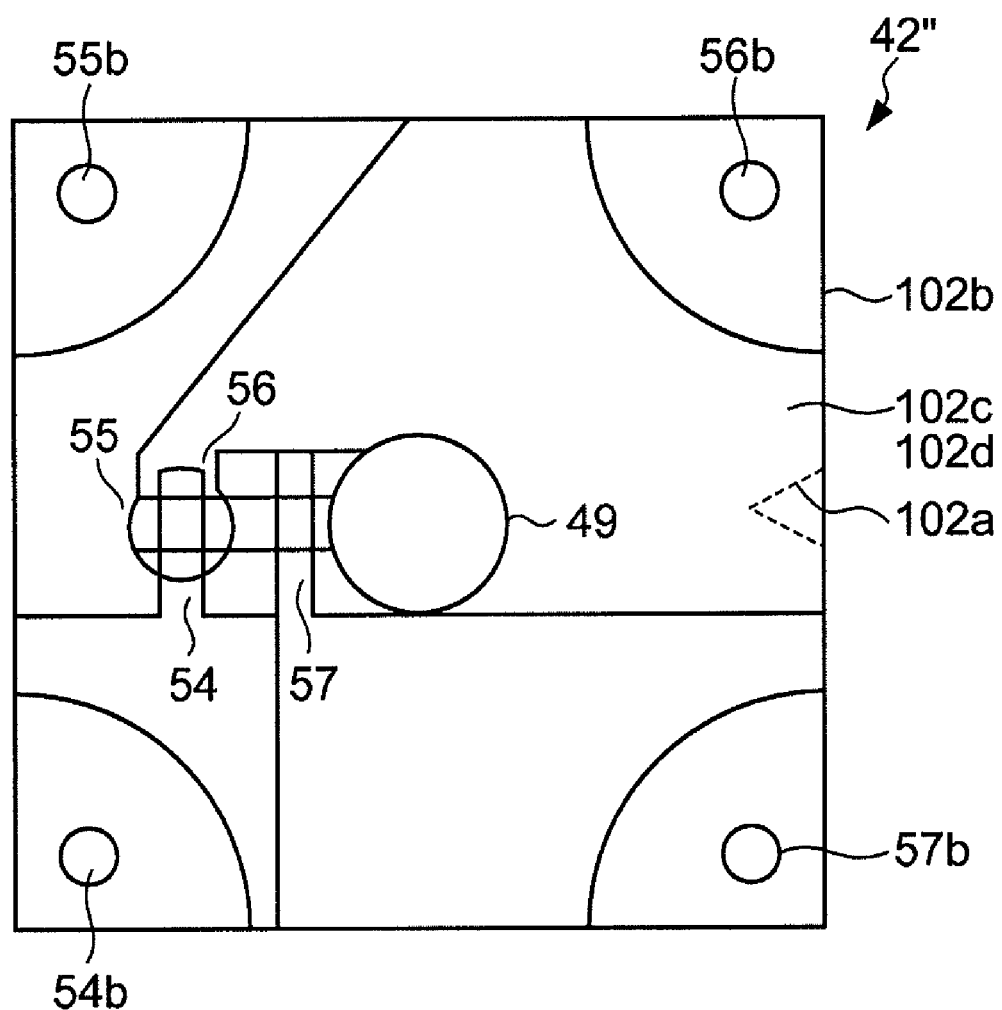
FIG. 10 is a transparent plan view of the blood sensor.

FIG. 10 is a transparent plan view of square-shaped blood sensor 42'. The outer shape of blood sensor 42" shown in FIG. 10 is a square, and the outer shape may be a polygonal such as a hexagon and octagon. By forming blood sensor 102 in a square or hexagonal shape, the material yield rate improves. Further, as shown in FIG. 11, aligning concave part 102a for aligning blood sensor unit 44 may be provided in one of the four sides, and the blood sensor may have an asymmetrical shape. Concave part 102a serves as the reference when blood sensor 42" is attached to blood sensor unit 44. Further, by positioning adapter 40 using convex part 130f (see FIG. 18) on the side of blood sensor unit 44 that engages with concave part 102a as a reference, detection electrodes 54 to 57 can be specified even if reference electrode 56d is not provided.

Contact parts 54b to 57b are provided in the corners of square-shaped substrate 102b. Spacer 102c and cover 102d are stacked on substrate 102b. Substrate 102b corresponds to substrate 46, spacer 102c corresponds to spacer 47, and cover 102d corresponds to cover 48 (see FIG. 5).

An Exploded Plan View of the Blood Sensor

The assembly and material of blood sensor 42 (see FIG. 5) provided in the blood test apparatus of the present invention will be described. The same components will be assigned the same reference numerals for ease of explanation.

Figure 11A:
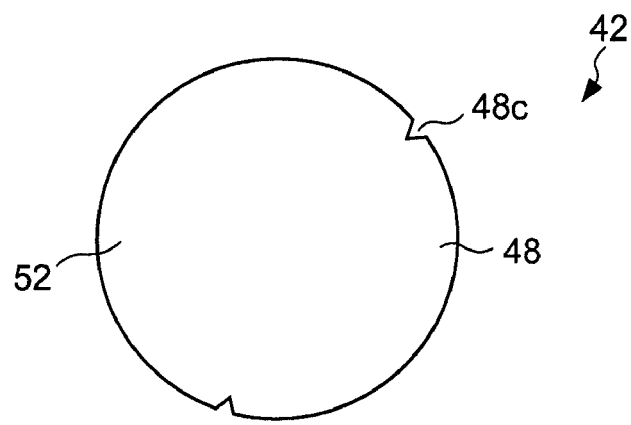
FIG. 11A shows a plan view of the cover.
Figure 11B:
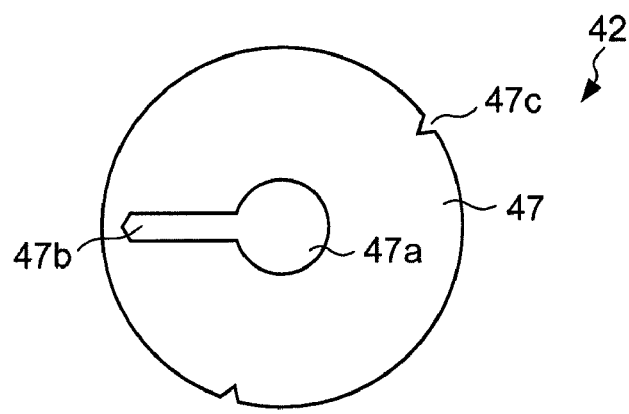
FIG. 11B shows a plan view of the spacer.
Figure 11C:
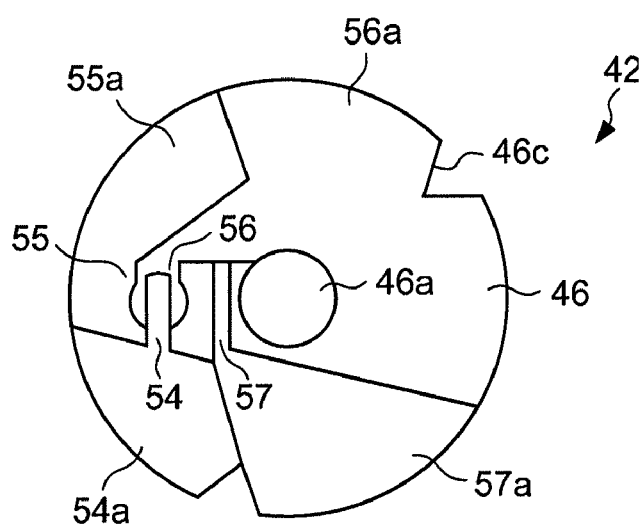
FIG. 11C shows a plan view of the substrate.

FIG. 11 is an exploded plan view of blood sensor 42. FIG. 11A is a plan view of cover 48, FIG. 11B is a plan view of spacer 47, and FIG. 11C is a plan view of substrate 46.

FIG. 11C is a plan view of round substrate 46 constituting blood sensor 42. The diameter of substrate 46 may be approximately 8.0 mm. The material of substrate 46 is resin such as polyethylene terephthalate (PET), and its thickness may be 0.075 to 0.250 mm (for example, 0.188 mm).

On the upper face of substrate 46, detection electrodes 54 to 57, connection electrodes 54a to 57a derived from detection electrodes 54 to 57, respectively, are formed in an integrated manner. These detection electrodes and connection electrodes may be formed through laser processing a conductive layer which is formed using the sputtering method or the vapor deposition method, wherein a material of the conductive layer can be gold, platinum or palladium.

The diameter of hole 46a provided near the center of substrate 46 may be approximately 2.0 mm. Preferably, the wall surface of hole 46a is less hydrophilic than supply channel 50 or is less water-repellent than upper face 48a of cover 48.

Hole 46a is preferably formed by punching press substrate 46 from the side of detection electrodes 54 to 57 with convex mold, because it is less likely to damage detection electrodes 54 to 57. Even if a burr is produced in hole 46a by this punching, the burr is oriented downward (toward the skin). Therefore, blood 16 is prevented from flowing out from storing part 49. Aligning concave part 46c provided at the outer periphery of substrate 46 engages with a aligning convex part (not shown) formed in holder 41 of blood sensor unit 44. The position where blood sensor 42 is attached to blood sensor unit 44 is thereby determined.

FIG. 11B is a plan view of spacer 47. The diameter of spacer 47 may be approximately 5.2 mm. The material of spacer 47 may be resin such as polyethylene terephthalate, and its thickness may be 0.025 to 0.25 mm (for example, 0.1 mm).

The diameter of hole 47a provided near the center of spacer 47 is 2.0 mm, and hole 47a is provided at the position corresponding to hole 46a provided in substrate 46. Preferably, the wall surface of hole 47a is less hydrophilic than supply channel 50 or is less water-repellent than upper face 48a of cover 48. Storing part 49 is constituted with hole 46a and hole 47a.

Slit 47b is formed toward the outer periphery from hole 47a. Slit 47b serves as blood supply channel 50. The wall surface of slit 47b and the upper face of substrate 46 meeting the wall surface of slit 47b are subjected to hydrophilic treatment. The width of slit 47b may be approximately 0.6 mm, and the length may be approximately 2.4 mm. As a result, the volume of supply channel 50 is approximately 0.144 µL. By making the volume of supply channel 50 small, test can be performed with a small amount of blood, so that the load on the patient becomes light and the patient does not feel fear.

Concave part 47c for aligning provided on the outer periphery of spacer 47 is formed on the position corresponding to concave part 46c for aligning provided in substrate 46.

FIG. 11A is a plan view of cover 48. The diameter of cover 48 may be approximately 5.2 mm. The thickness of cover 48 may be approximately 0.050 to 0.125 mm (for example, 0.075 mm).

Cover 48 can be made of a material that does not absorb laser light. Examples of the material of cover 48 include glass and plastic such as polyimide. If laser light is not absorbed in cover 48, the laser light can pass through ceiling face 49a of storing part 49 and puncture the skin. The laser light does not perforate ceiling face 49a, and so blood does not flow out from the hole, and blood 16 does not flow into apparatus body 39.

Cover 48 may be made of a material that absorbs laser light. In this case, cover 48 may be perforated by emitted laser light, or a hole through which emitted laser light pass may be formed in cover 48 before laser light is emitted.

Air hole 52 is provided to correspond to the tip part of supply channel 50. The diameter of air hole 52 is 50 μm.

Upper face 48a (see FIG. 5) of cover 48 that forms the upper face of substrate 45 is preferably subjected to water-repellency treatment. The ceiling face of supply channel 50 is preferably subjected to hydrophilic treatment. Further, preferably, ceiling face 49a of storing part 49 is subjected to milder hydrophilic treatment than supply channel 50 or is subjected to milder water-repellency treatment than upper face 48a of cover 48.

Hydrophilicity may be reduced by, for example, removing the hydrophilic agent applied on a hydrophobic member and increasing hydrophobicity. The hydrophilic agent is removed by, for example, decomposing the hydrophilic agent through UV (ultraviolet ray) irradiation. Ceiling face 49a of storing part 49 itself can be hydrophobic member.

The material may be made water repellent by mixing a water-repellent agent in the material. Further, the material may be made water-repellent by applying an appropriate amount of water-repellent agent on the surface of the hydrophilic member. The level of water-repellency may be adjusted by adjusting the amount of the water-repellent agent mixed.

The hydrophilicity or water-repellency of the components of blood sensor 42 can be adjusted as follows. Upper face 48a of cover 48 is subjected to water repellency treatment in advance. On the other hand, the overall lower face of cover 48 is subjected to hydrophilic treatment. The lower face of cover 48 includes the ceiling face of supply channel 50. Next, substrate 46, spacer 47 and cover 48 are stacked. After stacking, the hydrophilic agent of upper face 49a may be dissolved and removed by radiating short-wavelength UV through the opening of storing part 49. By manufacturing blood sensor 42 as described above, it is possible to make upper face 48a of cover 48 water-repellent and make the inner face of supply channel hydrophilic. Further, the inner face of storing part 49 may be less hydrophilic than supply channel 50 and less water-repellent than upper face 48a.

The ratio of the thickness of substrate 46 (0.188 mm), the thickness of spacer 47 (0.100 mm) and the thickness of cover 48 (0.075 mm) is approximately, 2.5:1.3:1. Storing part 49 that can pool a sufficient amount of blood can be formed while making blood sensor 42 thinner. Further, by the thickness of spacer 47 (0.100 mm), the effect of capillary action in supply channel 50 can be obtained sufficiently.

In blood sensor 42, the ratio of the volume of storing part 49 (0.904 μL) and the volume of supply channel 50 (0.144 μL) may be approximately 6:1, but the ratio is not particularly limited. Therefore, an incorrect test is not caused by running short of blood 16. Further, the volume of storing part 49 is not too large with respect to the volume of supply channel 50 required, and a large amount of blood 16 does not flow into supply channel 50 and does not wash away reagent 53 (see FIG. 5). Therefore, the rate of flow of blood 16 becomes constant, which does not generate variation in concentration of reagent 53, so that it is possible to examine blood 16 accurately.

Further, the amount of blood 16 collected is set a very small amount which is a sufficient amount required for a test of blood 16, and only blood 16 of approximately six times the volume of the supply channel is collected. Therefore, the load on the patient is reduced significantly. In view of the collection amount of blood 16 for accurate measurement and the collection amount of blood 16 for reducing the load on the patient, the volume of storing part 49 is preferably more than five times and less than seven times the volume of supply channel 50.

The Blood Sensor Unit

The blood sensor is preferably included in a blood sensor unit that can be attached to and removed from the apparatus body. That is, the blood sensor can be replaced in the apparatus body as one member of the blood sensor unit.

The Blood Sensor Unit that Uses a Needle as a Puncturing Means

Figure 12:
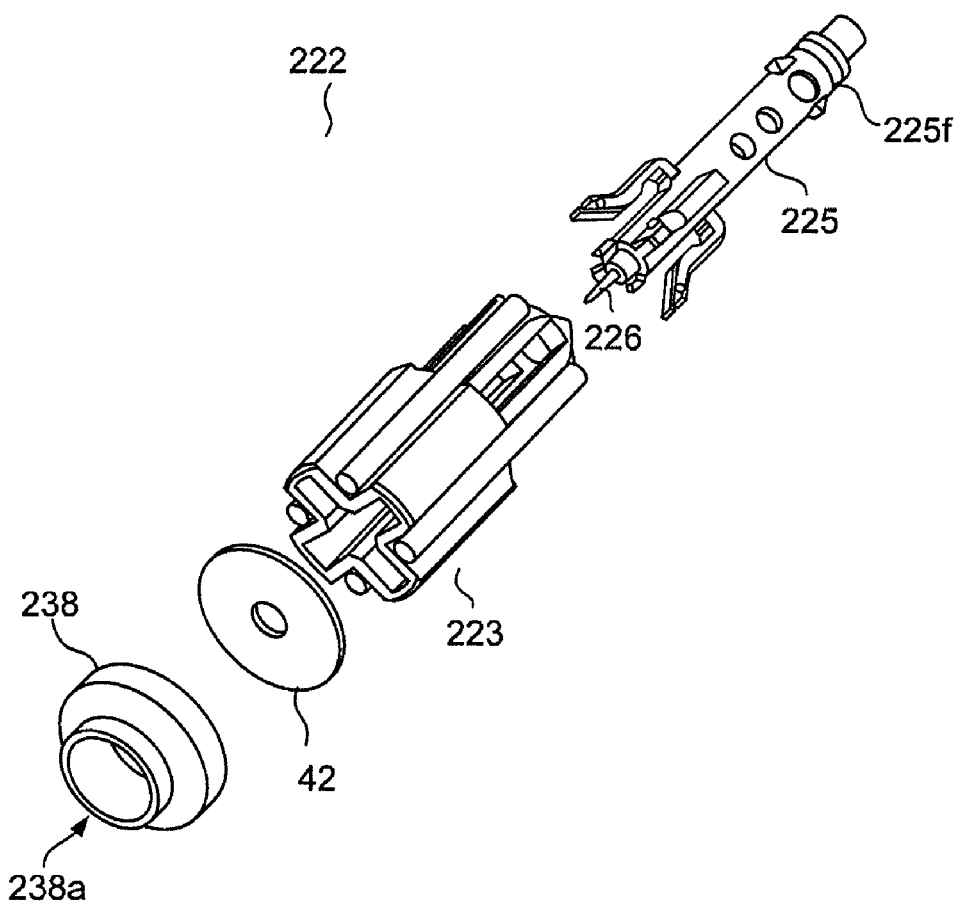
FIG. 12 is an exploded plan view of the blood sensor unit of the blood test apparatus with a needle as the puncturing means.

The blood sensor unit of the blood test apparatus that uses a needle as the puncturing means preferably includes, for example, a needle in addition to the blood sensor. FIG. 12 is an exploded perspective view of an example of blood sensor unit 222 of the blood test apparatus (see FIG. 1) that uses a needle as the puncturing means. Blood sensor unit 222 shown in FIG. 12 has second holder 238, holder 223, blood sensor 42, lancet 225 and blood collection needle 226. Lancet 225 and blood collection needle 226 are formed in an integrated manner so as not to disjoin easily. On the other hand, holder 223 and lancet 225 may be integrated after being manufactured separately, and may be separable from each other. The skin to be punctured comes to tip 238a of second holder 238. As described later, an absorbing means is placed in tip 238a.

FIG. 1 shows a state where plunger 230 is pulled backward, and blood collection needle 226 is inside blood sensor unit 222. That is, FIG. 21A shows a state before puncturing. To puncture the skin of the patient, plunger 230 pulled backward is made to project forward, and blood collection needle 226 is made to project from blood sensor 42. Plunger 230 is pulled backward again after puncturing, and blood collection needle 226 is accommodated in blood sensor unit 222. Except for the state where plunger 230 projects forward, blood collection needle 226 is accommodated in blood sensor unit 222, so that blood collection needle 226 does not puncture the skin by error and is secure, and, furthermore, does not make the patient feel fear.

The Blood Sensor Unit that Uses Laser Light as the Puncturing Means

The blood sensor unit of the blood test apparatus using laser light as the puncturing means may have a blood sensor.

Figure 13:
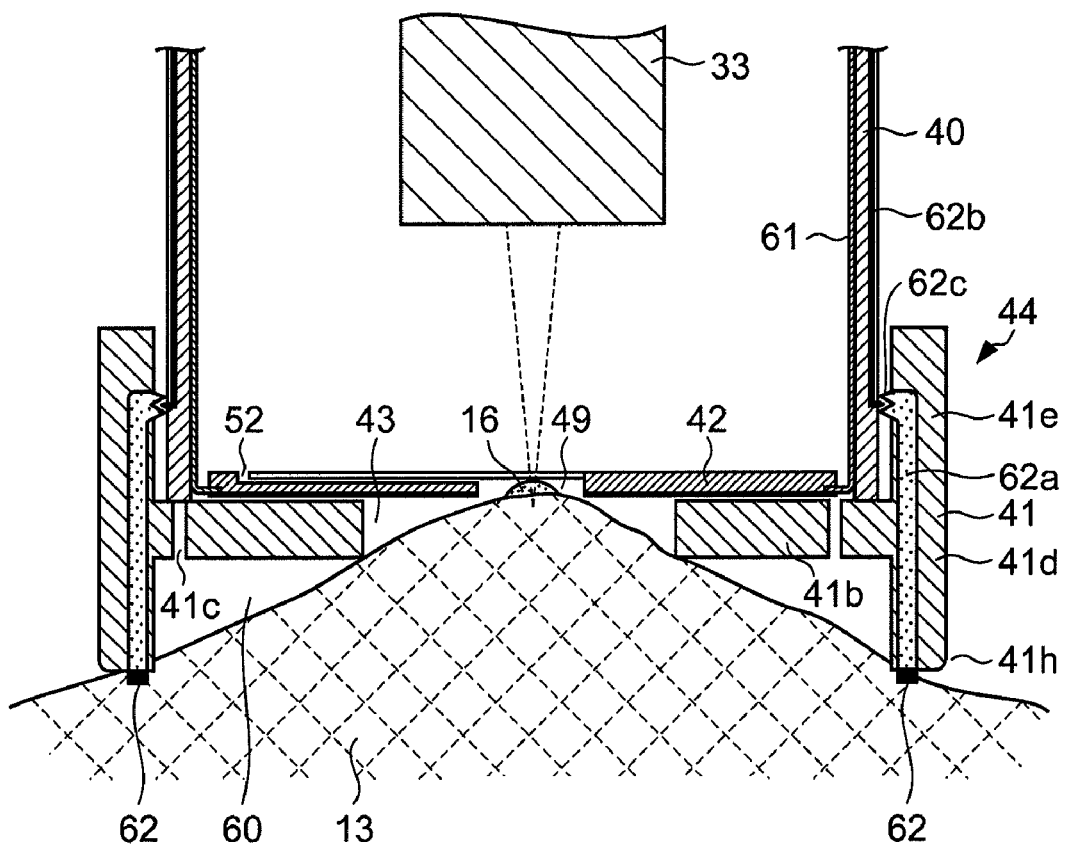
FIG. 13 is a cross-sectional view near the blood sensor unit of the blood test apparatus with laser light as the puncturing means.

FIG. 13 is a cross-sectional view of blood sensor unit 44 and the neighborhood of blood sensor unit 44. The cross section of blood sensor unit 44 is configured in the shape of "H" by cylinder-shaped holder 41 that opens upward and downward and attaching part 41b that is provided so as to seal the interior of holder 41.

The material of holder 41 is preferably resin that is applicable to injection molding, including ABS resin, AS resin and thermoplastic resin such as polyethylene, polypropylene, polyvinyl chloride and polyethylene terephthalate, or thermosetting resin such as phenol resin, epoxide resin and silicon resin.

Blood sensor 42 is attached to attaching part 41b, alternatively blood sensor 42 can be attached removably. In FIG. 13, blood sensor 42 is attached to an upper side (on the side of laser emitting apparatus 33) of attaching part 41b, alternatively blood sensor 42 may be attached to a lower side (on the side of the skin to be punctured) of attaching part 41b.

In the center of attaching part 41b, window 43 is preferably provided so as to correspond to storing part 49. The area of the opening part of window 43 is preferably larger than the area of the opening part of storing part 49. Further, negative pressure path 41c that penetrates the upper side and the lower side of attaching part 41b is provided. Negative pressure path 41c may be provided, for example, between the outer periphery of blood sensor 42 and the inner periphery of holder 41.

Cylindrical body 41d located below attaching part 41b forms negative pressure chamber 60 with skin 13. Further, the inner wall of cylindrical body 41e located above attaching part 41b of blood sensor unit 44 is latched outside adapter 40.

Connector 61 is provided inside adapter 40. Connector 61 includes a plurality of (for example, five) individual connectors 61a to 61e. When blood sensor unit 44 is attached to adapter 40, connectors 61a to 61e contact with contact parts 54b to 57b and 56c of blood sensor 42, respectively. Signals of connectors 61a to 61e are led to electrical circuit section 36.

First skin contact sensor 62 provided in tip part 41h of holder 41 detects skin 13 when blood sensor unit 44 abuts on skin 13. First skin contact sensor 62 also connects to connection part 62c provided in adapter 40 via conductor 62a arranged inside holder 41, and further connects to conductor 62b on the side of adapter 40. Conductor 62b is led to electrical circuit section 36.

A plurality of (for example, two) conductors constituting first skin contact sensor 62 are preferably provided in different positions in tip part 41h of holder 41 (in FIG. 13, on a straight line that passes the center of holder 41). By measuring the resistance value between the two conductors of first skin contact sensor 62, skin 13 is detected when blood sensor unit 44 abuts on skin 13. Therefore, it is possible to detect skin 13 when the tips of blood sensor unit 44 abut on skin 13 completely without space. Laser light is preferably not allowed to emit unless first skin contact sensor 62 detects a contact with the skin. First skin contact sensor 62 may be a mechanical micro switch or a reflection optical switch.

By emitting laser light from laser emitting apparatus 33, blood capillaries in skin 13 are damaged by the laser light, and blood 16 flows out. The out-flowing blood 16 is stored in storing part 49.

Figure 14:
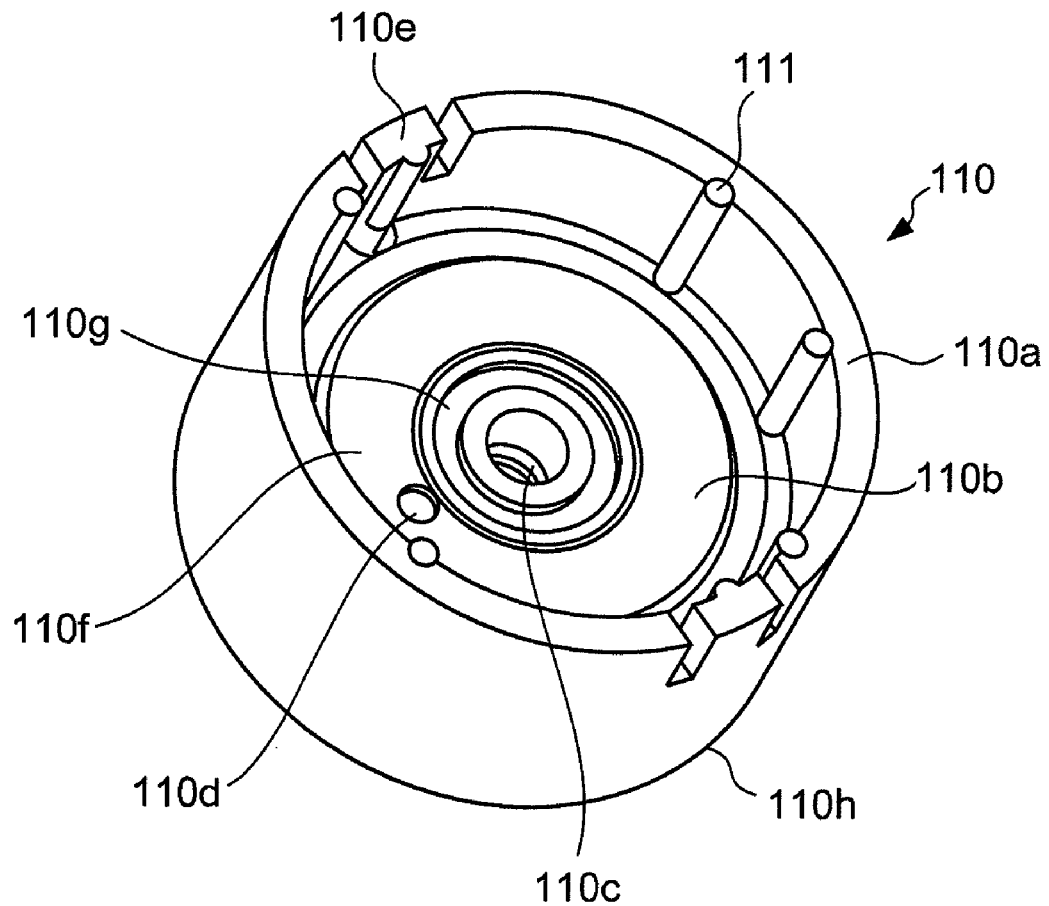
FIG. 14 is a perspective view showing the blood sensor unit of the blood test apparatus with laser light as the puncturing means.

FIG. 14 is a diagrammatic perspective view of blood sensor unit 110. Blood sensor unit 110 may have the same structure as blood sensor unit 44 unless described otherwise. Blood sensor unit 110 has the shape of a cylinder, and its cross section has the shape of "H." Five connectors 111 that transmit signals of the contact part of the blood sensor to electrical circuit section 36 may be provided inside holder 110a of blood sensor unit 110 (in the case of blood sensor 102, four connectors may be provided). Connector 111 connects to adapter 40 at an upper end of holder 110a and is led to electrical circuit section 36 via this adapter 40. Connector 111 may be provided in the adapter and may be connected with the contact part of the blood sensor of blood sensor unit 110.

Blood sensor 42 is attached on the reverse side (on the side of lower end part 110h, that is, on the side the skin to be punctured is placed) of attaching part 110b provided so as to seal the opening of holder 110a. Window 110c provided near the center of attaching part 110b is provided so as to correspond to the position of storing part 49 of blood sensor 42. Laser light passes through window 110c and storing part 49, and punctures skin 13.

Air hole 110d provided in attaching part 110b is provided in the position corresponding air hole 52 of blood sensor 42. Air hole 110d is provided to flow blood 16 into supply channel 50 of blood sensor 42 or create a negative pressure in storing part 49.

Blood sensor unit 110 engages with adapter 40 by the elasticity of engaging part 110e which engages with adapter 40. Two engaging parts 110e that face each other are provided in holder 110a. Engaging parts 110e have slits on both sides and thereby have elasticity, and are formed integrated with holder 110a. Therefore, engaging parts 110e can be made at a low cost.

Deodorizer storage 110f is provided on the upper face of attaching part 110b in a concentric fashion. A deodorizer is placed on deodorizer storage 110f. When the skin is punctured with laser light, cases occur where skin 13 is carbonized and produces an odor. This odor can be deodorized with the deodorizer. Further, blood pool 110g is provided on the upper face of attaching part 110b in a concentric fashion. Even if blood 16 overflows through hole 103b of blood sensor 42-2 (see FIG. 12), blood 16 stays in blood pool 110g, so that it is possible to prevent blood 16 from contaminating the body part of blood test apparatus 31.

Figure 15:
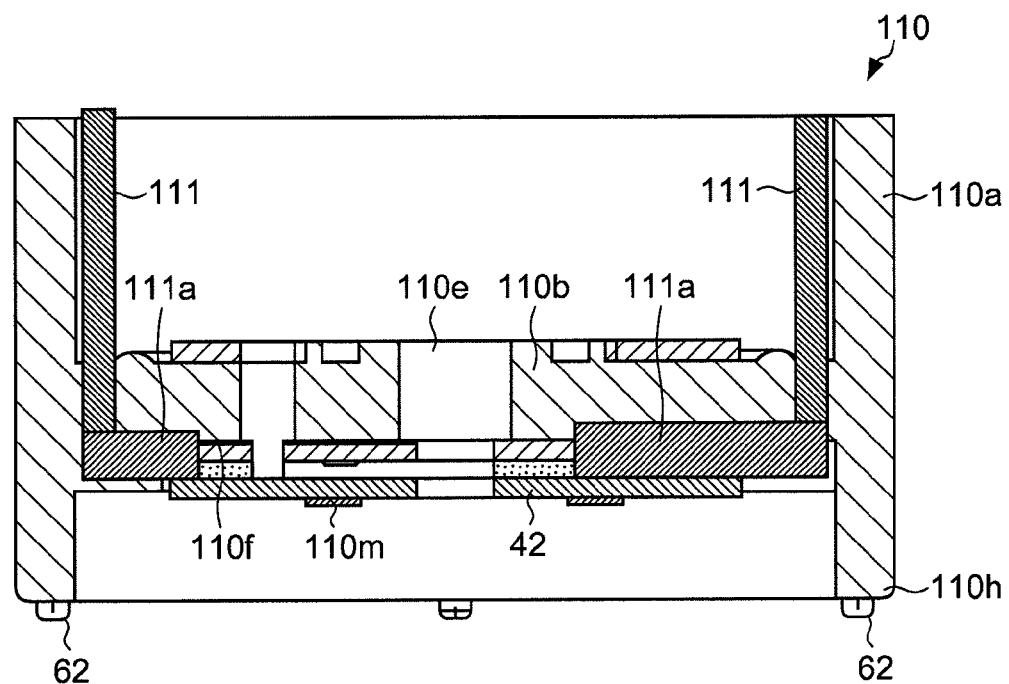
FIG. 15 is a cross-sectional view of the blood sensor unit of the blood test apparatus with laser light as the puncturing means.

FIG. 15 is a cross-sectional view of blood sensor unit 110. As shown in FIG. 15, blood sensor 42 is arranged in the lower face of attaching part 110b of blood sensor unit 110 and is held by attaching part 110b. Skin 13 is lifted by a negative pressure means (see 34 in FIG. 2, for example) and is in close contact with blood sensor 42. Blood sensor 42 is held by attaching part 110b, and so is less likely to be distorted by skin 13 that is in close contact with blood sensor 42. Connectors 111 contact with contact parts 54b to 57b and 56c of blood sensor 42. Guide part 63 (see FIG. 31) for guiding adapter 40 is preferably provided in holder 110a.

Connectors 111 are incorporated in holder 110a and formed so as to cut into part of attaching part 110b. Connectors 111 contact with blood sensor 42 in contact surface 111a. That is, the connection electrodes formed on the upper face of blood sensor 42 connect with contact parts (not shown) provided in connectors ill. Further, the connection electrodes of the blood sensor may connect with connectors ill via a conductive pattern or conductor joint section formed in the holder.

The blood test apparatus of the present invention has a negative pressure means, and the negative pressure means create a negative pressure inside blood sensor unit 110. As a negative pressure path, groove 110f may be formed in attaching part 110b of blood sensor unit 110. Groove 110f extends to window 110e formed near the center of attaching part 110b, from the outer periphery side of the attaching part of holder 110a. When a negative pressure is created, a negative pressure is also created in groove 110f, and blood sensor 42 is in close contact with attaching part 110b. When the negative pressure is released to the atmosphere, blood sensor 42 is removed from attaching part 110b.

Second skin contact sensor 110m may be provided in the lower face of blood sensor 42. Skin 13 is detected when skin 13 abuts on second skin contact sensor 110m by the negative pressure in negative pressure chamber 60. The second skin contact sensor may be configured with, for example, a counter electrode. Laser light emission is preferably not allowed unless second skin contact sensor 110m detects a contact with the skin. Negative pressure means 34 may stop creating a negative pressure in negative pressure chamber 60 when second skin contact sensor 110m is detected to be abutted on skin 13. By controlling negative pressure means 34 in this way, negative pressure means 34 can be controlled without wasting the negative pressure power. Further, first skin contact sensor 62 may be provided in lower end part 110h of holder 110a.

Figure 16:
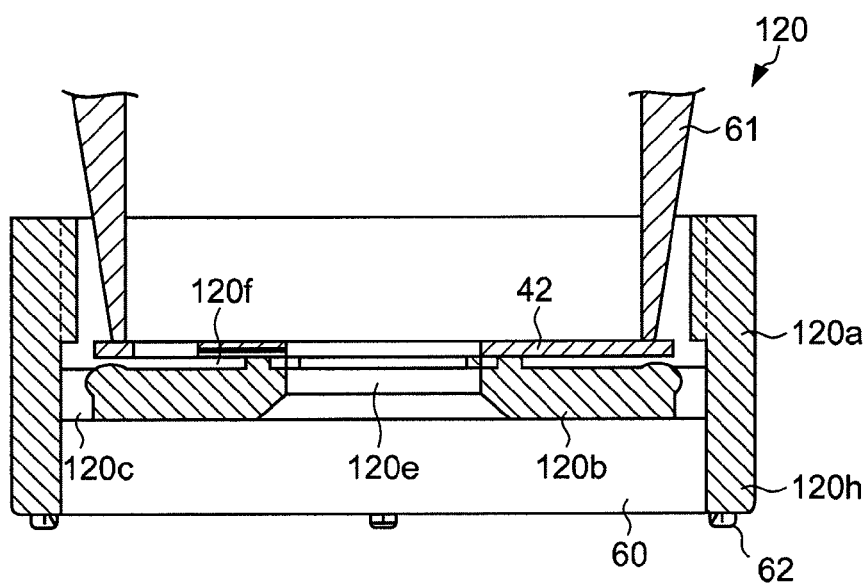
FIG. 16 is a cross-sectional view of the blood sensor unit of the blood test apparatus with laser light as the puncturing means.

FIG. 16 is a cross-sectional view of blood sensor unit 120. Blood sensor unit 120 may have the same structure as blood sensor unit 110 unless described otherwise. Blood sensor unit 120 is different from blood sensor unit 110 in that blood sensor 42 is mounted on the upper side of attaching part 120b formed so as to seal the opening of holder 120a. Connectors 61 connected to electrical circuit section 36 conduct with contact parts (54b to 57b and 56c) of blood sensor 42.

The upper space and the lower space in attaching part 120b of blood sensor unit 120 having an H-shaped cross section, communicate through negative pressure path 120c. The lower space forms negative pressure chamber 60. First skin contact sensor 62 is provided in lower end 120h of holder 120a. Further, second skin contact sensor 120m may be provided in the lower face of attaching part 120b.

By attaching blood sensor 42 on the upper face of attaching part 120b, it is possible to make contact pressures between connectors 61 and the contact parts (54b to 57b and 56c) of the blood sensor larger. Further, it is possible to attach blood sensor 42 to attaching part 120b in a simple manner.

Separated by blood sensor 42 and attaching part 120b, the space on the side of the apparatus body (the upper space in the figure) and the space on the side of skin 13 (the lower space in the figure), communicate with each other via negative pressure path 120c. To create a negative pressure on skin 13, it is possible to create a negative pressure in the space on the side of skin 13 via this negative pressure path 120c. Further, when a negative pressure is released to the atmosphere, airflows into space on the side of apparatus body 39 quickly via negative pressure path 120c. Therefore, it is possible to prevent blood led in blood sensor 42 from splashing inside of apparatus body 39.

Groove 120f may be formed on the upper side of attaching part 120b as a negative pressure path. Groove 120f extends from the outer periphery of attaching part 120b of holder 120a to window 120e formed near the center of attaching part 120b. Providing groove 120f makes it unnecessary to provide a hole which penetrates attaching part 120b.

Figure 17:
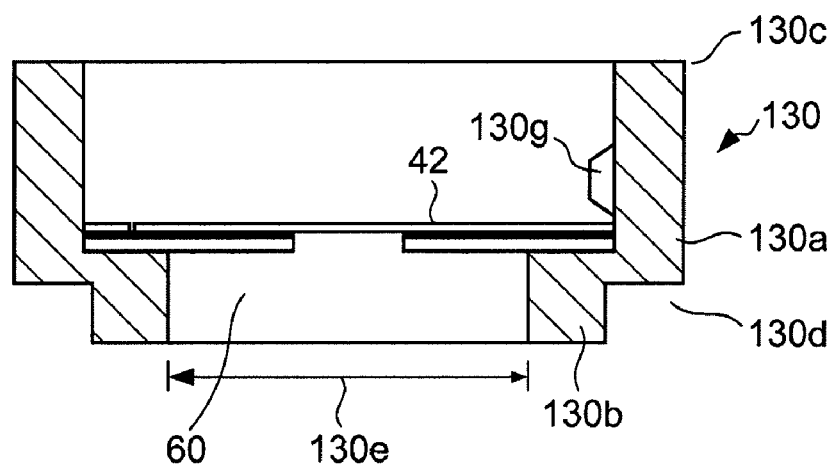
FIG. 17 is a cross-sectional view of the blood sensor unit of the blood test apparatus with laser light as the puncturing means.

FIG. 17 is a cross-sectional view of blood sensor unit 130. Blood sensor unit 130 may have the same structure as blood sensor unit 44 unless described otherwise. Here, blood sensor 42 is attached in the upper face of attaching part 130b of blood sensor unit 130. The inner diameter of lower end 130d of holder 130a is smaller than the inner diameter of upper end 130c.

The diameter of opening part 130e of negative pressure chamber 60 formed on the lower side of attaching part 130b is preferably 2 to 20 mm, more preferably 3 to 10 mm, and even more preferably 5 to 7 mm, so that a negative pressure is created on the skin to be punctured more efficiently. Further, by making the outer shape of lower end 130d smaller than the outer shape of upper end 130c, it is possible to stack a plurality of blood sensor units 130 vertically and accommodate blood sensor units 130 efficiently. On the other hand, blood sensor 42 needs to have a certain size, and so the outer shape of upper end 130c is difficult to be made smaller.

Further, locking convex part 130g provided inside holder 130a so as to project toward blood sensor 42, latches blood sensor 42 and prevents blood sensor 42 from being removed from holder 130a.

Figure 18:
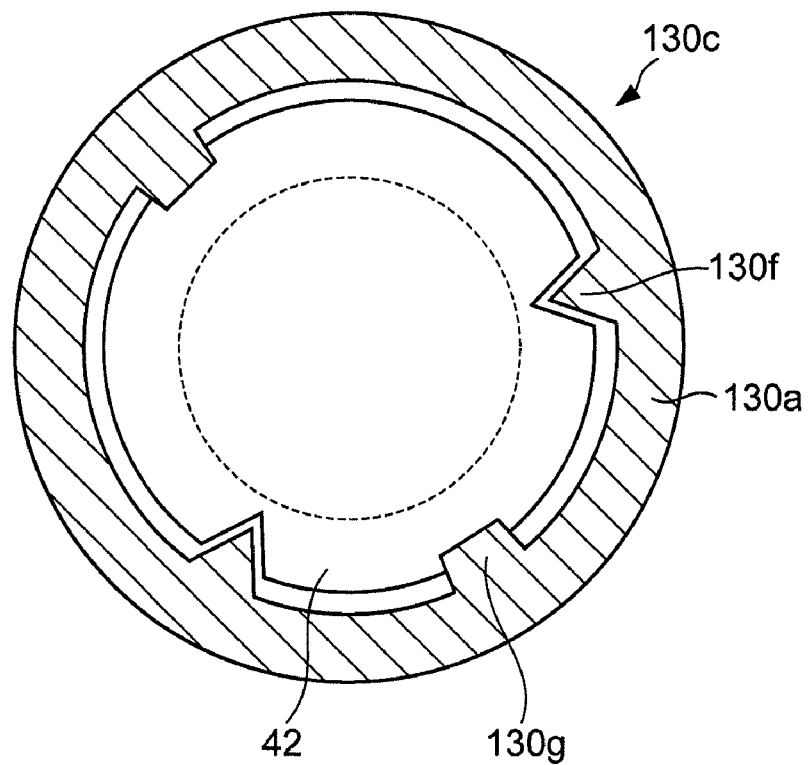
FIG. 18 is a plan view showing the blood sensor unit of the blood test apparatus with laser light as the puncturing means.

FIG. 18 is a plan view of blood sensor unit 130. Two convex parts 130f that fit concave parts 46c and 47c (see FIG. 9) for aligning blood sensor 42 are formed in holder 130a of blood sensor unit 130. Two convex parts 130f are arranged in the positions approximately 120 degrees apart from each other. The position where blood sensor 42 is arranged in blood sensor unit 130 is determined by convex part 130f of holder 130a and aligning concave part 46c of blood sensor 42. Blood sensor unit 130 in which blood sensor 42 is arranged adequately is attached to adapter 40 in a predetermined position by guide part (see FIG. 26). As a result, signals of detection electrodes 54 to 57 of blood sensor 42 can be transmitted to electrical circuit section 36. Further, there may be only one convex part 130f. When there is one convex part 130f, holder 130a preferably adopts a structure that allows blood sensor 42 to be fit in attaching part 130b.

The Tip of the Blood Sensor Unit

FIG. 19 to FIG. 23 are cross-sectional views of a first embodiment near lower end part 110h of holder 110a. Lower end part 110h abuts on skin 13 of the patient, and a groove is formed in part of lower end part 110h. Lower end part 110h shown in FIG. 19 to FIG. 22 is formed with two concentric lines 110j. The groove formed between two or more concentric lines 110j is made capillary 110x, so that over-sampled blood after measurement (which has flown out by puncturing, but cannot be guided in blood sensor 42) can be sucked into the capillary.

Figure 19:
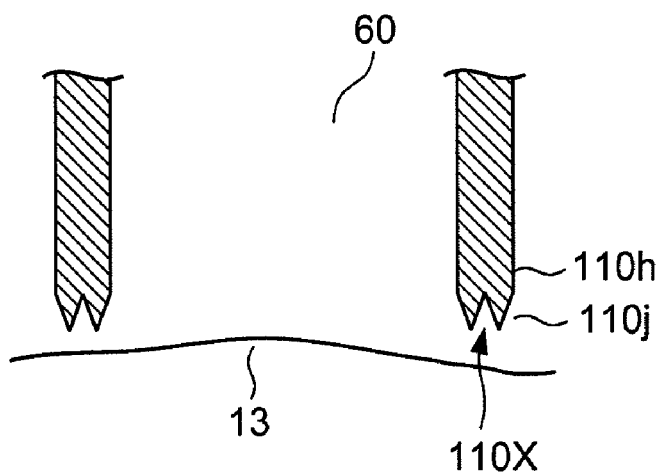
FIG. 19 shows a tip part of the blood sensor unit where grooves, which serve as capillaries, are formed at the tips.
Figure 20:
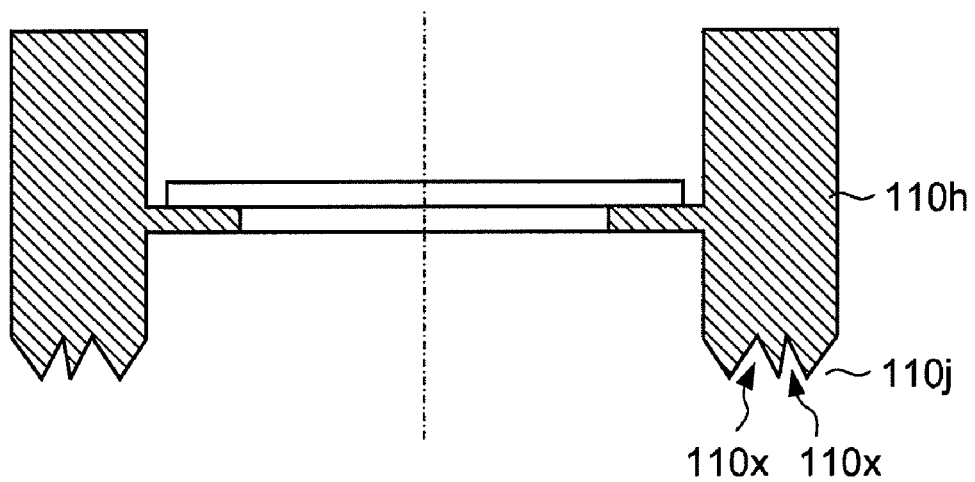
FIG. 20 shows a tip part of the blood sensor unit where grooves, which serve as capillaries, are formed at the tips.

There may be one capillary 111x formed with concentric lines 110j as shown in FIG. 19 or there may be a plurality of capillaries 111x as shown in FIG. 20. The degrees of projection of each concentric line 110j may be the same with each other. Alternatively, when line 110j on the outer periphery side is made more projecting than line 110j on the inner periphery side, blood that remains on skin inside holder 110a is sucked in capillary 111x easily. Embodiments shown in FIG. 21 and FIG. 22 provide the same effects as this.

Figure 21:
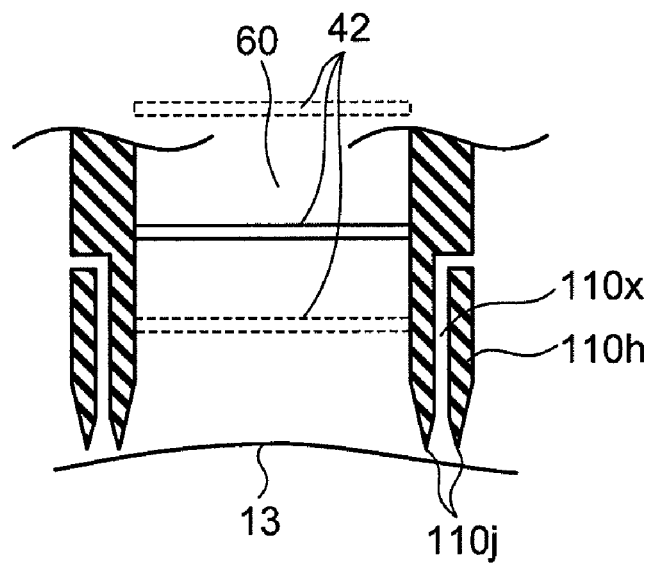
FIG. 21 shows a tip part of the blood sensor unit where grooves, which open at the both ends and serve as capillaries, are formed at the tips.
Figure 22:
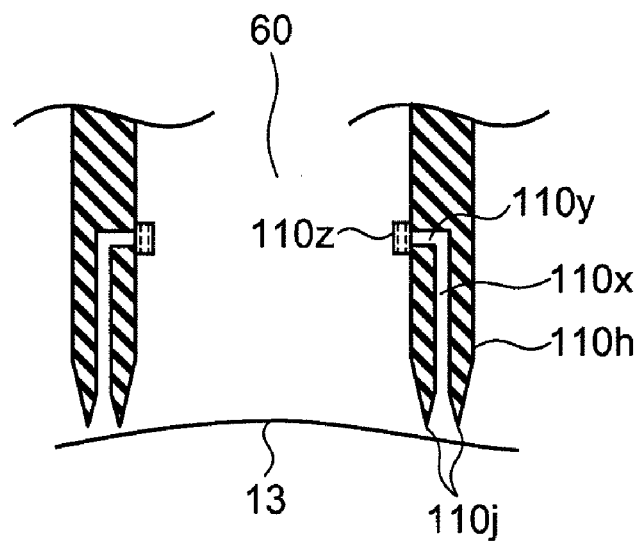
FIG. 22 shows a tip part of the blood sensor unit where grooves, which open at both ends and serve as capillaries, are formed at the tips.

Although, as shown in FIG. 19 and FIG. 20, capillary 110x may open only in one end, capillary 110x that opens in both ends as shown in FIG. 21 and FIG. 22 is preferable, because the performance of suction improves.

As shown in FIG. 21, the height setting position of blood sensor 42 from the skin surface may be adjusted appropriately. Skin 13 preferably contacts with blood sensor 42 when the negative pressure means creates a negative pressure in negative pressure chamber 60, so that blood is easily guided into blood sensor 42 and the focus of laser light can be adjusted easily by specifying the position of skin 13.

Part of the blood that flows out from the skin by puncturing, which has not been guided into the blood sensor, can be absorbed in capillary 110x formed in lower end part 110h. Therefore, it is not necessary to prepare paper for wiping off blood every test, and the usability improves.

Alternatively, when a negative pressure is created in negative pressure chamber 60 of the blood sensor unit, hole 110y can be provided as shown in FIG. 22, which hole 110y communicates between the capillary formed in lower end part 110h and negative pressure chamber 60. Blood 16 may be sucked in the capillary more efficiently by the negative pressure created in the negative pressure chamber. The exit of communicating hole 110y may be covered with filter 110z. Filter 110z prevents blood 16 sucked into the capillary from splashing into negative pressure chamber 60.

Further, when a negative pressure is created in negative pressure chamber 60 of the blood sensor unit of the present invention, negative pressure chamber 60 needs to be sealed, and so end 110h and skin 13 must be placed in close contact with each other. Therefore, by forming lower end part 110h with two concentric lines 110j which are made sharp at an acute angle (see FIG. 19 to FIG. 22), lower end part 110h contacts with skin 13 by line contact, and so negative pressure chamber 60 is sealed.

Figure 23A:
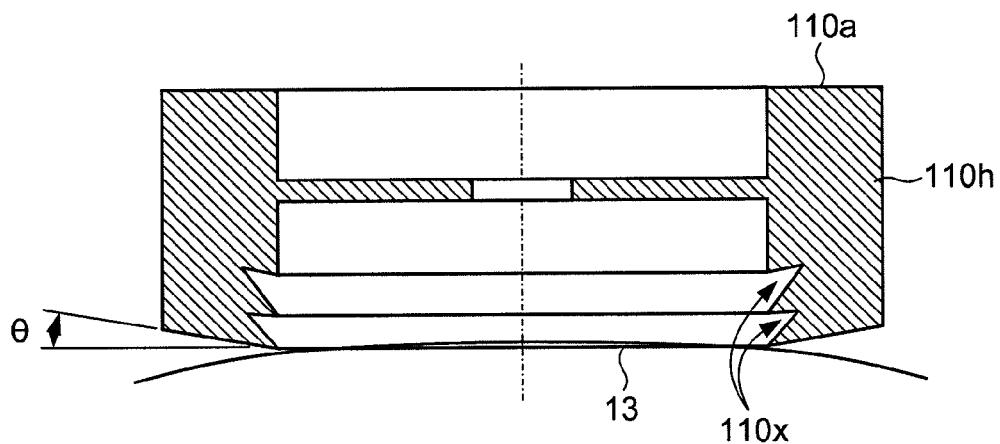
FIG. 23 shows a tip part of the blood sensor unit, where FIG. 23A has grooves formed on the inner face of the holder, and FIG. 23B has grooves formed on the outer face of the holder.
Figure 23B:
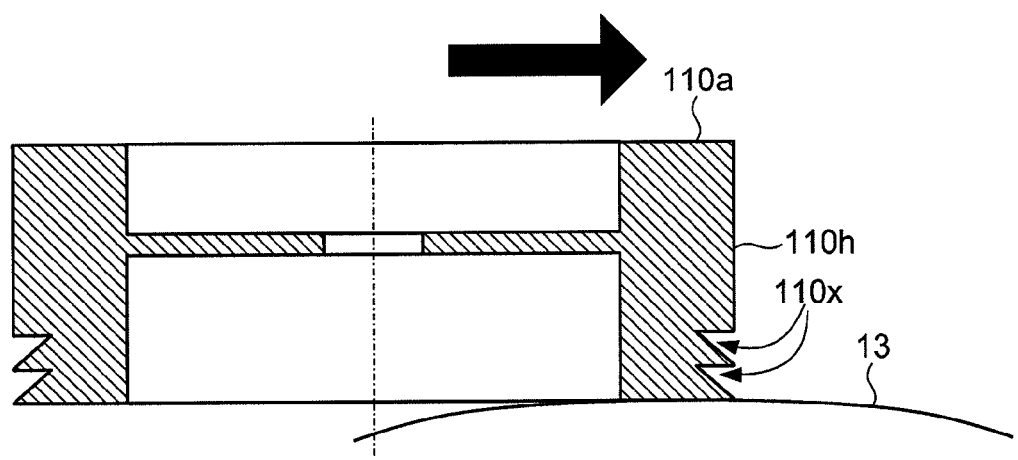

The example shown in FIG. 23A or FIG. 23B shows a case where groove 110x, which serves as a capillary, is provided in the inner face or the outer face of lower end part 110h of holder 110a. There are one or more grooves 110x. The shape of the groove is not limited as long as a capillary action is caused. In the case of FIG. 23A, the blood remaining on the skin inside holder 110a upon a blood test, is sucked into groove 110x located on the lower side of the inner face of holder 110*a*. The surface of lower end part 110*h* of holder 110*a*, which contacts with the skin, may be inclined with respect to the skin surface at an angle of θ (>0), so that lower end part 110*h* contacts with the skin byline contact and is more likely to bite into the skin upon wiping operation, which makes it possible to remove blood more reliably. FIG. 23B shows an example where groove 110*x* is provided in the outer face of lower end part 110*h* of holder 110*a*, which is preferable in a case that blood is wiped off by the blood sensor unit once removed from the skin after the blood collection. Grooves may be provided in both the inner face and the outer face of lower end part 110*h* of holder 110*a*.

Figure 24:
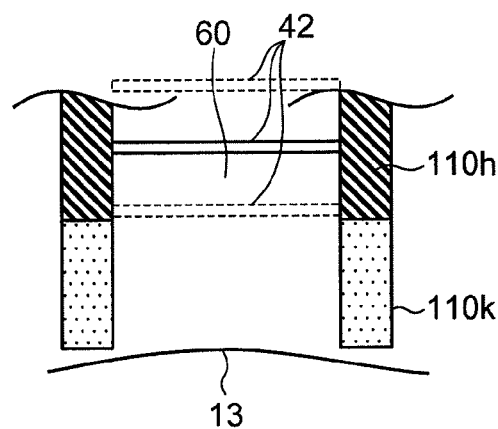
FIG. 24 shows a tip part of the blood sensor unit where an absorbing member is placed at the tip of the holder.

FIG. 24 to FIG. 27 are cross-sectional views showing a second embodiment near lower end part 110*h* of holder 110*a*. That is, an absorbing member is provided in lower end part 110*h*. As shown in FIG. 24, concentric abutting part 110*k* provided in lower end part 110*h* abuts on skin 13. By making abutting part 110*k* an absorbing member that is absorbent such as a sponge, blood 16 which has flown out from the skin by puncturing and has not been guided into the blood sensor, can be wiped off after measurement. Therefore a preparation for wiping paper, for example, is unnecessary and the usability of the blood sensor unit is improved. Further, if an antiseptic is added to the absorbing member, the absorbing member becomes sanitary.

As shown in FIG. 24, blood sensor 42 may be provided in lower end part 110*h*, and the height setting blood sensor 42 from the skin surface is adjusted as appropriate. Preferably, the skin is made to contact with blood sensor 42 when the negative pressure means creates a negative pressure in negative pressure chamber 60.

Further, in a case that a negative pressure is created in negative pressure chamber 60 of the blood sensor unit of the present invention, abutting part 110*k* may be formed with an elastic body such as rubber, silicon, urethane and a sponge. Abutting part 110*k* abuts on skin 13 completely by its elasticity, and negative pressure chamber 60 is sealed. Further, by making abutting part 110*k* flat, the area where abutting part 110*k* abuts on skin 13 becomes large, and negative pressure chamber 60 is sealed reliably.

Figure 25:
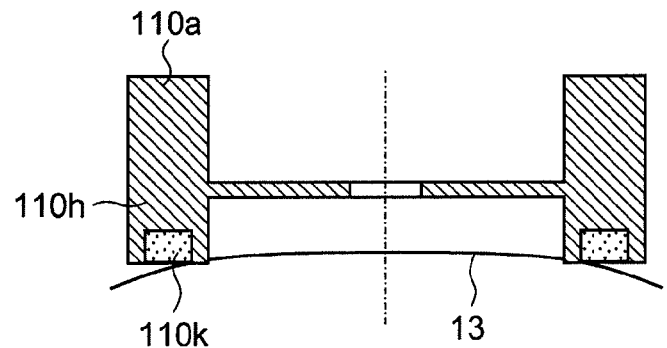
FIG. 25 shows a tip part of the blood sensor unit where the absorbing member is embedded inside the lower face of the holder.
Figure 26:
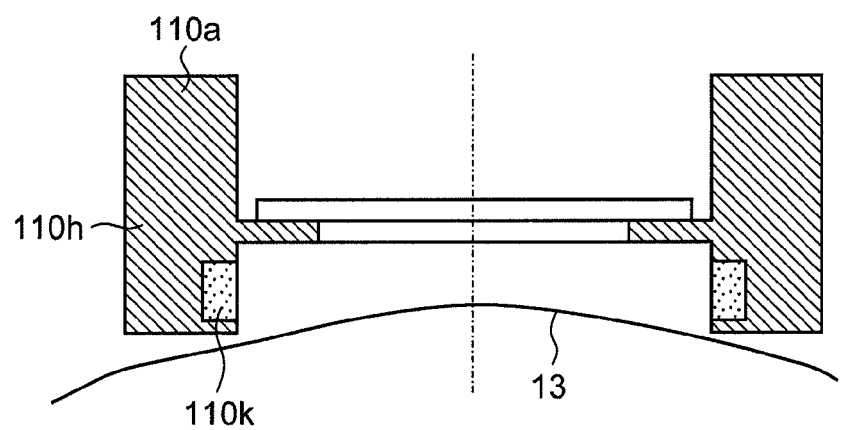
FIG. 26 shows a tip part of the blood sensor unit where the absorbing member is embedded inside the inner face of the holder.

In FIG. 25, absorbing member 110*k* that is an absorbing member having absorbability is embedded inside the surface of lower end part 110*h* of holder 110*a* that contacts with the skin. In FIG. 26, absorbing member 110*k* is embedded inside the inner surface of lower end part 110*h* of holder 110*a*. Alternatively, absorbing member 110*k* may be provided in the part of the corner (at the edge where the inner face intersects with the lower face) inside lower end part 110*h* of holder 110*a* (not shown).

Figure 27:
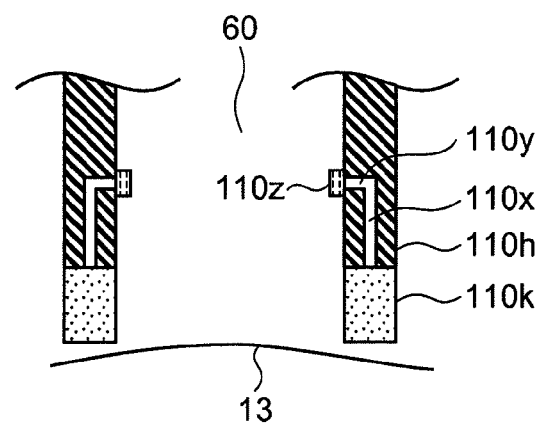
FIG. 27 shows a tip part of the blood sensor unit where the absorbing member is placed in the tip part of the holder and capillaries are formed in the lower end part.

Further, as shown in FIG. 27, it is also possible to form capillary 110*x* in lower end part 110*h* provided with abutting part 110*k*, and provide through hole 110*y* that communicates between capillary 110*x* and negative pressure chamber 60. The negative pressure in negative pressure chamber 60 makes it possible to suck excess blood 16 into capillary 110*x* more efficiently. Further, by covering with filter 110*z* the exit of communicating hole 110*y*, it is possible to prevent sucked blood 16 from splashing into negative pressure chamber 60.

Figure 28:
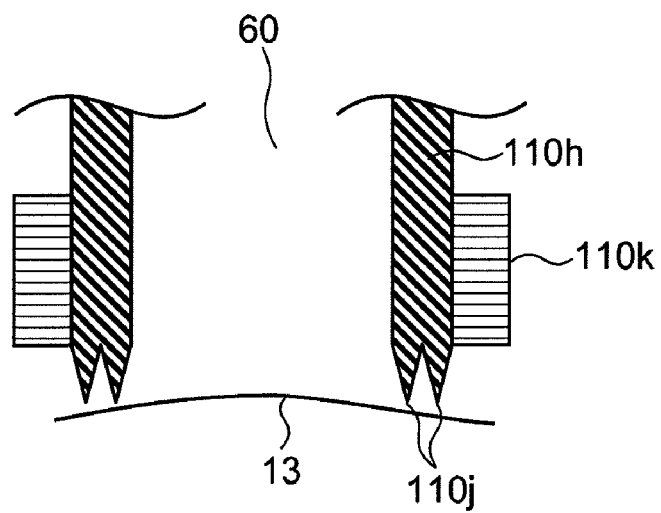
FIG. 28 shows a tip part of the blood sensor unit where the absorbing member is provided on the outer face of the holder.

FIG. 28 is a cross-sectional view showing a third embodiment near lower end part 110*h* of holder 110*a*. Absorbing member 110*k* that is made of an absorbent material such as fiber cotton, is provided in the outer face of lower end part 110*h*. Excess blood 16 flowing out by puncturing can be wiped off using absorbing member 110*k* after measurement, which makes preparation for wiping paper unnecessary and improves the usability. Further, if an antiseptic is added to the absorbing member, the absorbing member becomes sanitary.

Further, by forming lower end part 110*h* with two concentric lines 110*j* which are made sharp at an acute angle, lower end part 110*h* abuts on skin 13 firmly by line contact, and negative pressure chamber 60 is kept sealed.

Figure 29:
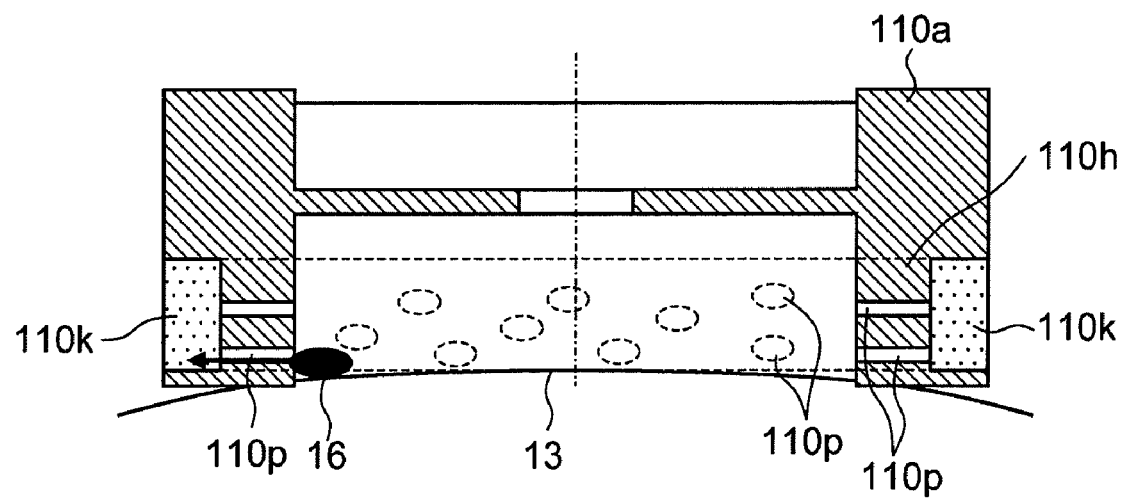
FIG. 29 shows a tip part of the blood sensor unit where the absorbing member is placed on the outer face of the holder and communicates with the interior of the holder via a through-hole.

FIG. 29 is a cross-sectional view of a fourth embodiment near lower end part 110*h* of holder 110*a*. Absorbing member 110*k* that is absorbent is provided in the outer face of lower end part 110*h*, and hole 110*p* is formed in lower end part 110*h* from inside of lower end part 110*h* so as to connect to absorbing member 110*k*. Absorbing member 110*k* is formed with materials such as fiber and spongy in a compressed state. Therefore, even when a negative pressure is created, air is less likely to pass through and leak in absorbing member 110*k*. Further, by making hole 110*p* a tiny hole (for example, having a pore diameter of 50 μm to 250 μm), capillary action is more likely to be caused. As described above, by combining breathing absorbing member 110*k* and hole 110*p* that causes capillary act ion, absorption performance of blood remaining on the skin in holder 110*a* improves. When hole 110*p* is provided in a horizontal direction, capillary action caused by hole 110*p* is less likely to be influenced by gravity, which improves absorption performance.

By providing a plurality of holes 110*p* in lower end part 110*h* of holder 110*a* radially centering around the punctured axis, absorption performance further improves. Further, a plurality of holes 110*p* may be vertically arranged. Negative pressure means 34 may also create a negative pressure inside holder 110*a* via a negative pressure path.

Figure 30A:
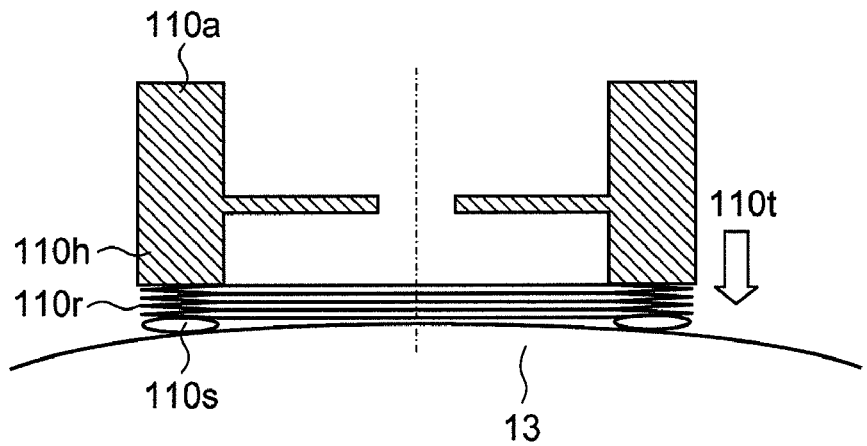
FIG. 30A shows a state where the extensible member pressed against the skin is contracted.
Figure 30B:
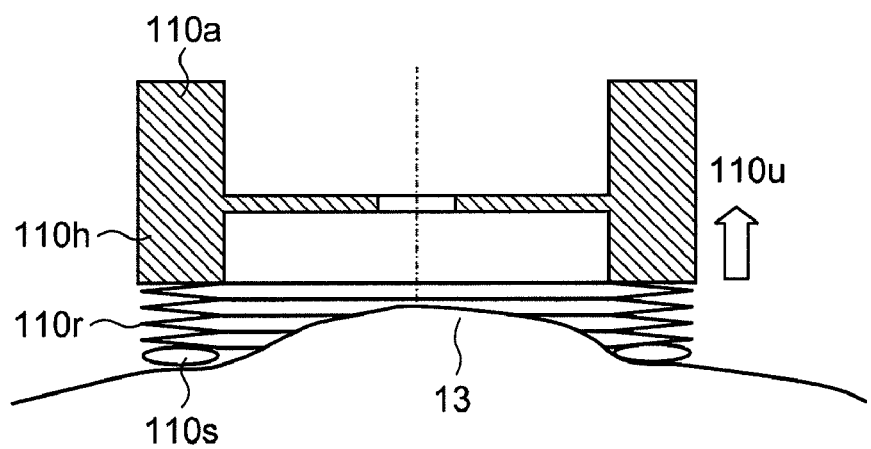
FIG. 30B shows a state where the extensible member is drawn upward and extended.
Figure 30C:
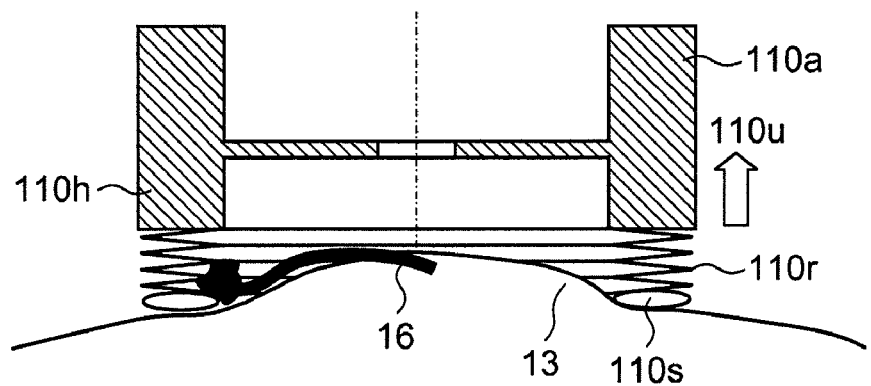
FIG. 30C shows a state where blood is guided into the extensible member.

FIG. 30A, FIG. 30B and FIG. 30C are cross-sectional views showing a fifth embodiment near lower end part 110*h* of holder 110*a*. In this example, accordion-shaped extensible member 110*r* is provided on the bottom face of lower end part 110*h*, and seal member 110*s* is provided in the tip part of extensible member 110*r*. Accordion-shaped extensible member 110*r* can extend and contract freely to some extent in a vertical direction in FIG. 30. Extensible member 110*r* keeps the inside of holder 110*a* airtight. By using a seal member such as a pad as seal member 110*s*, holder 110*a* contacts with skin 13 more tightly, so that the inside of holder 110*a* becomes more airtight.

FIG. 30A shows a state where the whole of blood sensor unit 110 including holder 110*a* is pressed against skin 13 (in the direction of arrow 110*t*). Accordion-shaped extensible member 110*r* is compressed with seal member 110*s* to be crushed. FIG. 30B shows a state where puncturing and measurement are completed and the whole of blood sensor unit 110 including holder 110*a* is moved in a direction that moves away from the skin (in the direction of arrow 110*u*). At this time, the airtightness between accordion-shaped extensible member 110*r* and seal member 110*s* produces a negative pressure in holder 110*a*, and skin 13 is lifted. Furthermore, when blood sensor unit 110 is moved in the direction of arrow 110*u*, as shown in FIG. 30C, blood 16 remaining inside holder 110*a* is absorbed in spaces in accordion-shaped extensible member 110*r*. Further, the blood once absorbed is maintained in member 110*r*.

In this way, if the inside of holder 110*a* is highly airtight, remaining blood 16 can be collected in a simple manner without a negative pressure inside. Blood 16 is disposed inside blood sensor unit 110, so that wiping paper does not have to be prepared, and the user can wipe off and dispose of the blood without smearing the user's hands.

Attachment of the Blood Sensor Unit

Figure 31:
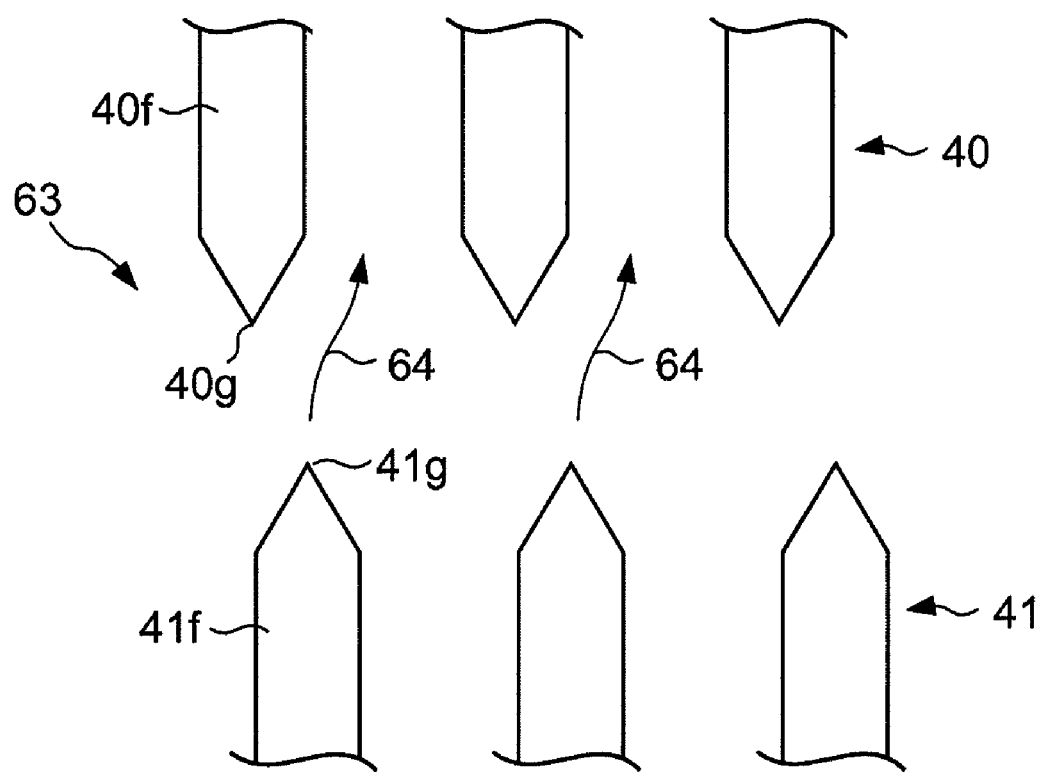
FIG. 31 is a developed plan view showing the primary part of a guide part for attaching the blood sensor unit to the blood test apparatus.

As described above, the blood sensor unit can be attached to and removed from the blood test apparatus. Therefore, a guide part for attaching the blood sensor unit easily may be provided in the blood sensor unit and a blood sensor unit attaching part in the apparatus body. For example, a guide part for attaching blood sensor unit 44 in a simple manner is provided in holder 41 of blood sensor unit 44 and adapter 40 in the blood test apparatus shown in FIG. 2. FIG. 31 is an exploded plan view of the primary part of guide part 63 that guides insertion of blood sensor unit 44 into adapter 40. Convex part 41*f* is formed inside holder 41, and convex part 40*f* is formed outside adapter 40. Tip part 41*g* and tip part 40*g*, which are the tips of convex part 41*f* and convex part 40*f*, respectively, are made sharp. Tip part 41*g* and tip part 40*g* face each other. Convex part 40*f* and its tip part 40*g*, and convex part 41*f* and its tip part 41*g*, constitute guide part 63.

When blood sensor unit 44 is inserted into adapter 40, even when the positions of blood sensor unit 44 and adapter 40 are out of predetermined alignment, blood sensor unit 44 is inserted along guide part 63 while correcting the course (see arrow 64). As a result, connectors 61*a* to 61*e* provided in adapter 40 are sure to contact with contact parts 54*b* to 57*b* and 56*c* provided in blood sensor 42, respectively. Therefore, blood sensor unit 44 can be inserted without taking into account the rotation angle with respect to the axis of the insertion direction, so that blood sensor unit 44 can be attached in a simple manner.

Figure 32:
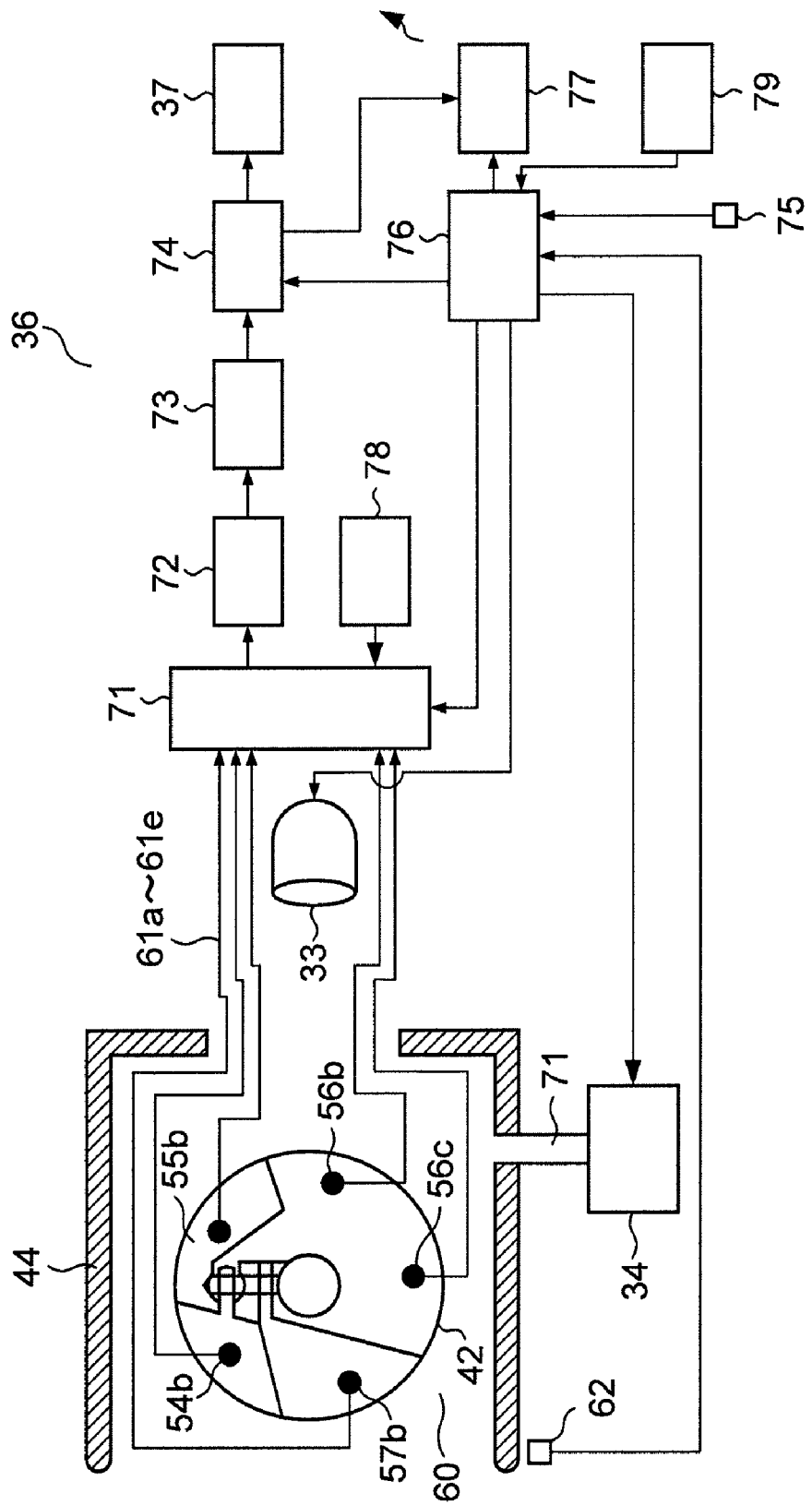
FIG. 32 is a block diagram showing an electrical circuit section of the blood test apparatus.

FIG. 32 is a block diagram showing an electrical circuit section in the blood test apparatus that uses laser light as the puncturing means. In FIG. 32, 54*b* to 57*b* and 56*c* are contact parts formed in blood sensor 42. Contact parts 54*b* to 57*b* and 56*c* are connected to switch circuit 71 via connectors 61*a* to 61*e*. The output of switch circuit 71 is connected to the input of current/voltage converter 72. The output of converter 72 is connected to the input of calculating section 74 via analogue/digital converter (hereinafter A/D converter) 73. The output of calculating section 74 is connected to display section 37 formed with liquid crystal. Further, reference voltage supply 78 is connected to switch circuit 71. Reference voltage supply 78 may be a ground potential.

The output and input of controlling section 76 is connected to a control terminal of switch circuit 71, calculating section 74, puncture button 75, transmitting section 77, timer 79, laser emitting apparatus 33, negative pressure means 34 and first skin contact sensor 62, and also connected to a warning means (not shown) and a second skin contact sensor (see FIG. 15). Further, the output of calculating section 74 is also connected to the input of transmitting section 77. The output of negative pressure means 34 is led to inside negative pressure chamber 60 and blood sensor unit 44 via negative pressure path 41*c*.

The operation of electrical circuit section 36 will be described. Before a blood test, it is specified to which of connectors 61*a* to 61*e*, contact parts 54*b* to 57*b* and 56*c* of blood sensor 42 are each connected. First, by the command from controlling section 76, contact part 56*c* is specified out of connectors 61*a* to 61*e*, wherein electrical resistance between contact part 56*c* and the neighboring terminals is zero. A connection electrode connected to specified contact part 56*c* is determined as reference electrode 56*d*. Using connector 61 connected to contact part 56*c* as a reference, connectors 61 connected to connection electrodes 56*a*, 57*a*, 54*a* and 55*a*, are specified in order. In this way, connectors 61 each connected to connection electrodes 54*a* to 57*a* are specified.

Then, a blood test is conducted. Next, switch circuit 71 is switched, and detection electrode 54 as an active electrode for measuring the amount of blood components is connected to current/voltage converter 72 via connector 61. Further, detection electrode 54 which serves as a sensing electrode for detecting the inflow of blood 16 is connected to reference voltage supply 78 via connector 61. A certain voltage is applied between detection electrode 54 and detection electrode 55. When blood 16 flows into the detecting section in this state, a current flows between detection electrode 54 and detection electrode 55. This current is converted to a voltage by current/voltage converter 72, and the voltage value is converted to a digital value by A/D converter 73. The digital value is outputted to calculating section 74. Calculating section 74 detects a sufficient inflow of blood 16 based on the digital value.

When blood 16 is not detected with detecting section 51 after a predetermined time has passed or when the amount of blood 16 is not adequate, a warning means maybe started for warning, and the appropriate treatment may be displayed on display section 37.

Next, glucose, which is a blood component, is measured. The glucose content is measured by switching switch circuit 71 by the command of controlling section 76; and connecting detection electrode 54 to current/voltage converter 72 via connector 61, wherein the electrode 54 serves as the active electrode for measuring the glucose content. Further, detection electrode 56 is connected to reference voltage supply 78 via connector 61, wherein the electrode 56 serves as the counter electrode for measuring the glucose content.

For example, while the glucose in blood and the oxidation-reduction enzyme are reacted for a certain period, current/voltage converter 72 and reference voltage supply 78 are turned off. After a certain period (1 to 10 seconds) has passed, by a command from controlling section 76, a certain voltage (0.2 V to 0.5 V) is applied between detection electrode 54 and detection electrode 56. The current flowing between detection electrode 54 and detection electrode 56 is converted to a voltage by current/voltage converter 72. This voltage value is converted to a digital value by A/D converter 73. The digital value is outputted to calculating section 74. Calculating section 74 calculates the glucose content based on this digital value.

After the glucose content is measured, the Hct (hematocrit) level is measured. First, by the command from controlling section 76, switch circuit 71 is switched. Detection electrode 57, which serves as the active electrode for measuring the Hct level, is connected to current/voltage converter 72 via connector 61. Further, detection electrode 54, which serves as the counter electrode for measuring the Hct level, is connected to reference voltage supply 78 via connector 61.

Next, by the command from controlling section 76, a certain voltage (2V to 3V) is applied between detection electrode 57 and detection electrode 54. The current flowing between detection electrode 57 and detection electrode 54 is converted to a voltage by current/voltage converter 72. This voltage value is converted to a digital value by A/D converter 73. This digital value is outputted to calculating section 74. Calculating section 74 calculates the Hct level based on this digital value.

From the thus calculated Hct level and the glucose content, with reference to a calibration curve or a calibration table which has been obtained in advance, the glucose content is corrected with the Hct level. The corrected result is displayed on display section 37.

Further, the corrected result maybe transmitted from transmitting section 77 to an injection apparatus that injects insulin (as an example of a curative drug). The result maybe transmitted by radio, but is preferably transmitted using optical communication which does not interfere with medical equipment. If the injection apparatus can set the dose of insulin automatically based on the measured data transmitted to the injection apparatus, the patient does not have to set the dose of insulin to administer in the injection apparatus, which alleviates the inconvenience of the setting. Further, the dose of insulin can be set in the injection apparatus without involving an artificial means, so that it is possible to prevent setting errors.

Although the blood test apparatus of the present invention has been described referring to an example of measuring glucose, the blood test apparatus of the present invention is also applicable to measurement of blood components (such as the lactate level acid and cholesterol) other than glucose.

The Test Method

Figure 33:
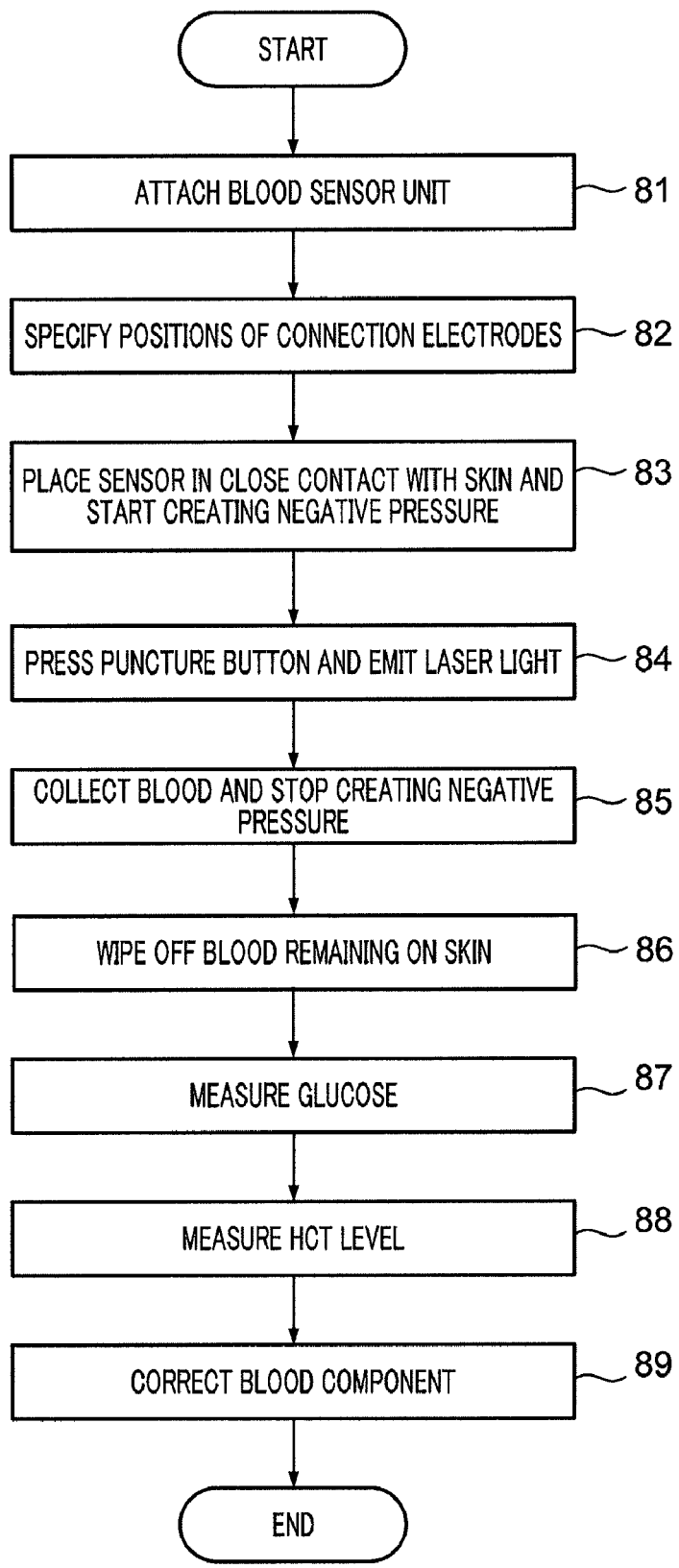
FIG. 33 is a flowchart of a blood test using the blood test apparatus.
Figure 34A:
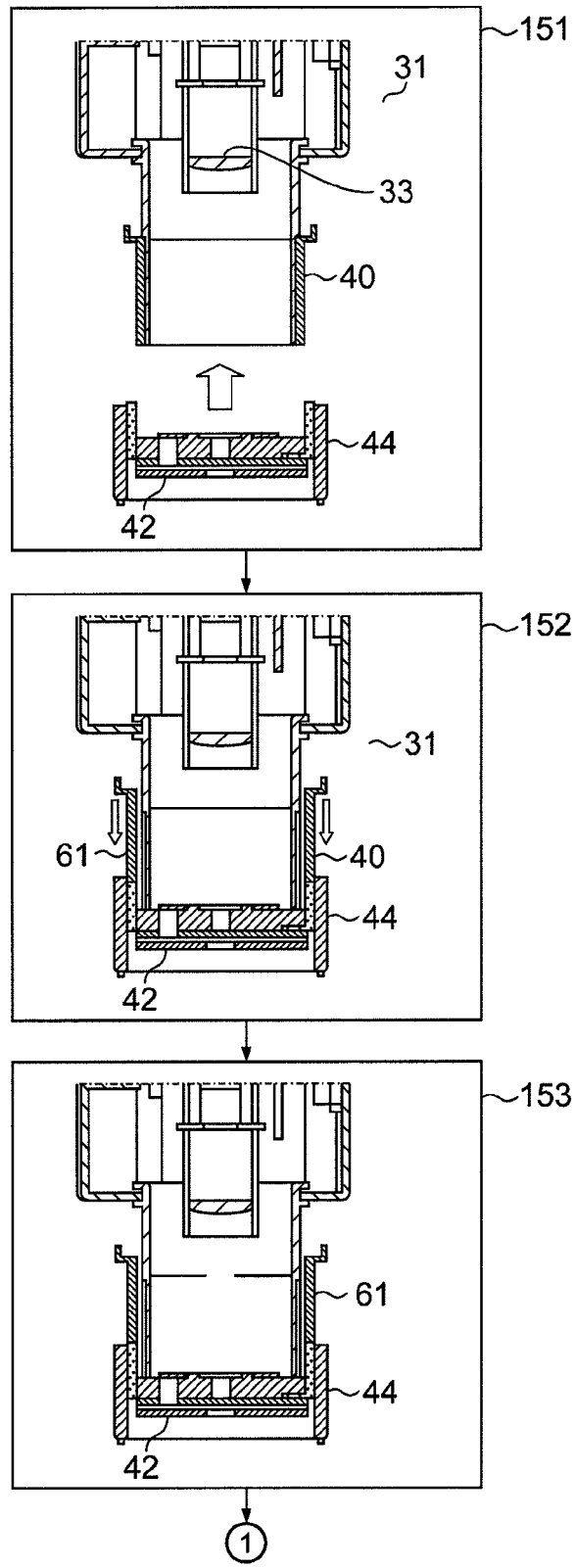
FIG. 34A is a cross-sectional view showing individual steps in an example of steps of a test using the blood test apparatus of the present invention more specifically.
Figure 34B:
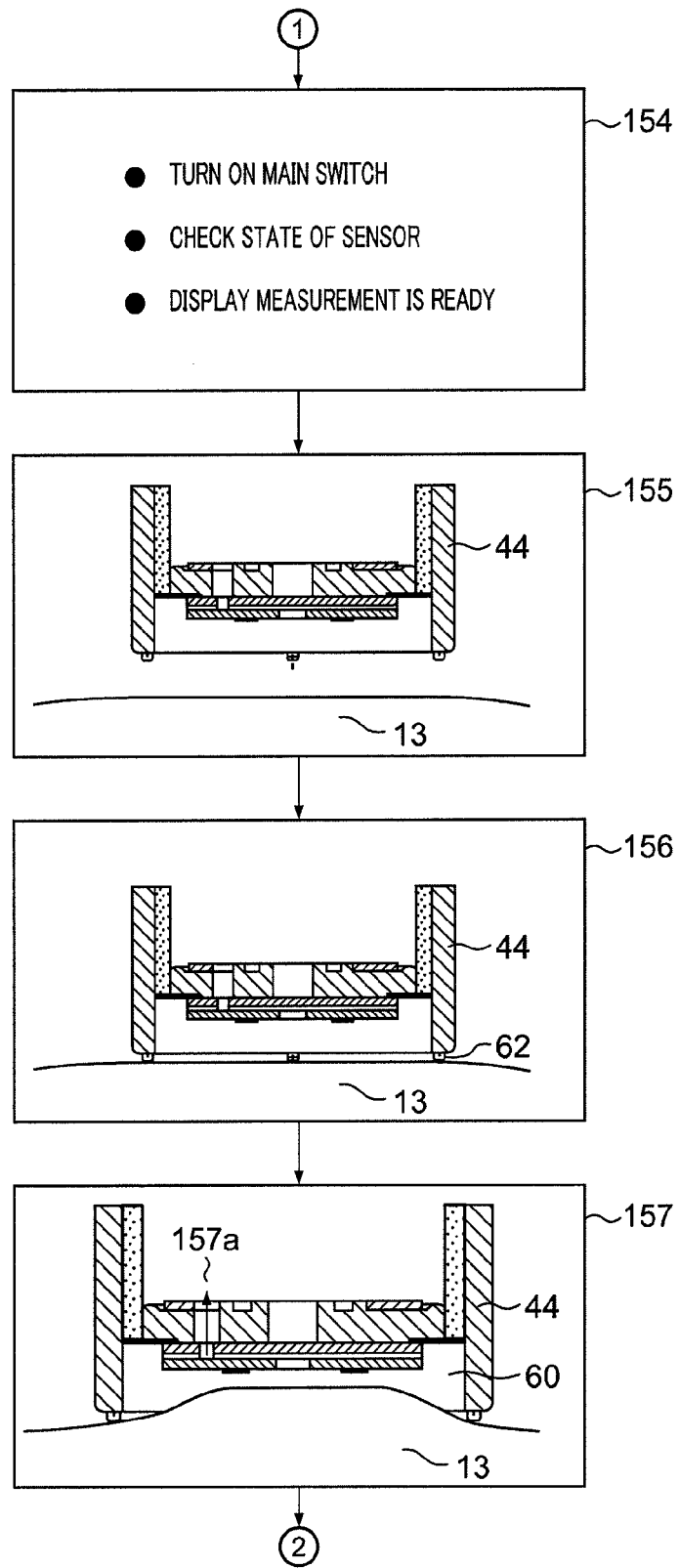
FIG. 34B is a cross-sectional view showing individual steps following FIG. 34A.
Figure 34C:
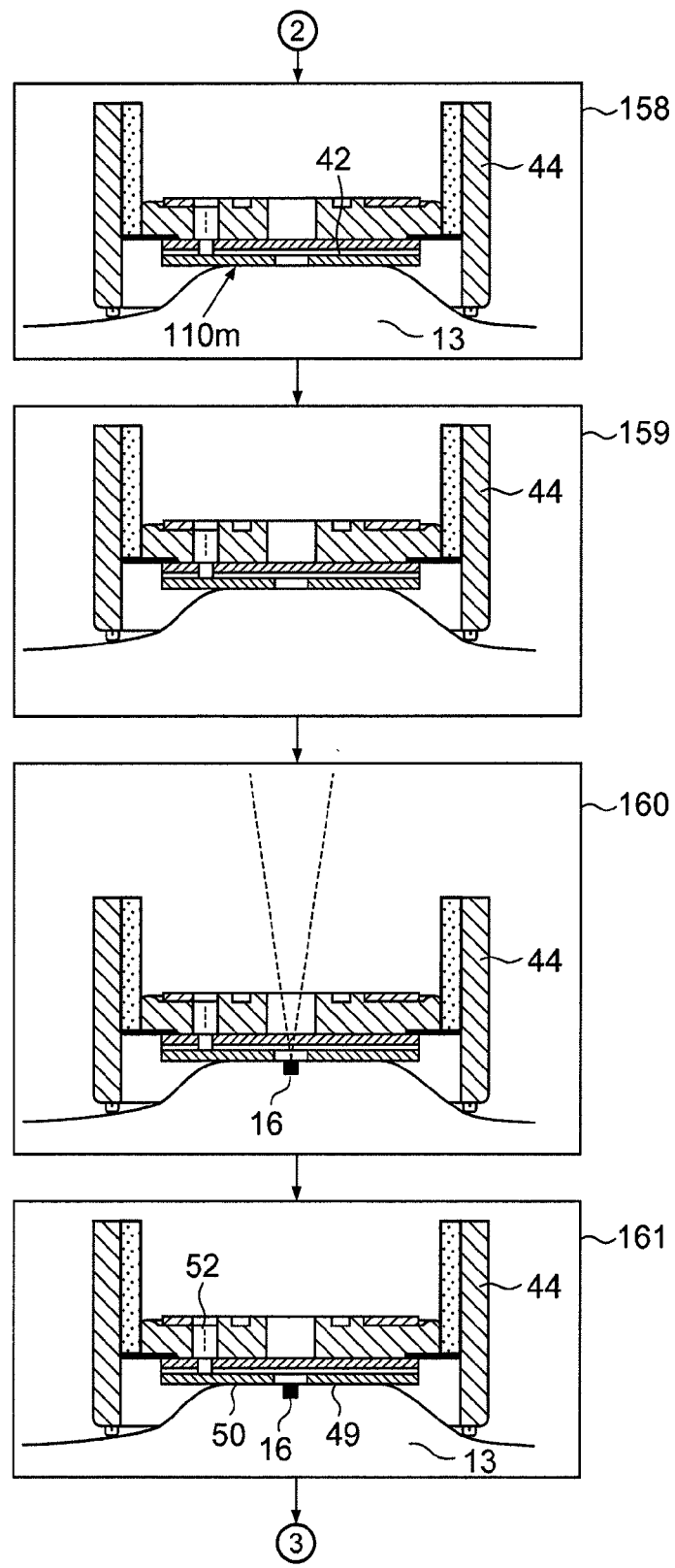
FIG. 34C is a cross-sectional view showing individual steps following FIG. 34B.
Figure 34D:
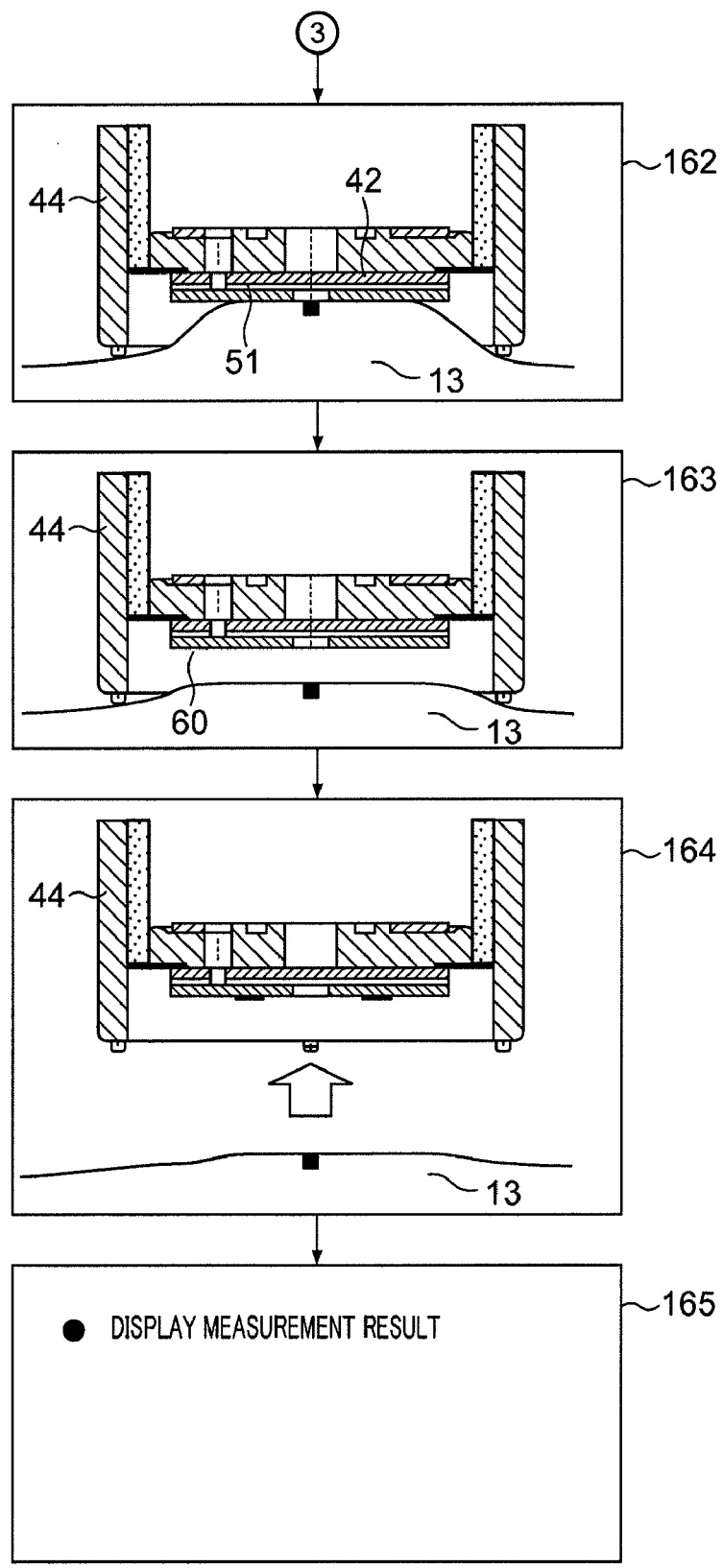
FIG. 34D is a cross-sectional view showing individual steps following FIG. 34C.

The steps of examining blood with the blood test apparatus of the present invention will be described below referring to an example of the blood test apparatus with laser light as the puncturing means. The flow of a blood test using blood test apparatus 31 shown in FIG. 2 will be described with reference to FIG. 33. Blood sensor unit 44 is attached to blood test apparatus 31 (step 81). In this step 81, blood sensor unit 44 is inserted into adapter 40. By this insertion, the tip of adapter 40 abuts on attaching part 41b of blood sensor unit 44. Blood sensor unit 44 is latched to adapter 40 by the elasticity of holder 41.

Next, connection electrodes 54a to 57a of blood sensor 42 are each specified (step 82). Here, reference electrode 56d is specified from resistance values between each neighboring connectors 61a to 61e by electrical circuit section 36. From specified reference electrode 56d, connection electrodes 56a, 57a, 54a and 55a are specified in a clockwise order. In this way, connection electrodes 54a to 57a of the blood sensor of blood sensor unit 44 inserted at an arbitrary angle are each specified in step 82, and, as a result, detection electrodes 54 to 57 are specified.

Next, tip part 41h of holder 41 in blood sensor unit 44 is pressed against skin 13 of the patient and is placed in close contact with skin 13 (step 83). When first skin contact sensor 62 detects a contact between skin 13 and tip part 41h, suction pump 34a of negative pressure means 34 operates and starts creating a negative pressure. It is also possible to detect the load current to be applied to suction pump 34a by controlling section 76, and display on display section 37 whether or not the negative pressure is enough for puncturing. It is possible to measure a predetermined time from creating a negative pressure with timer 79 and display on display section 37 whether puncturing is allowed or not, instead of detecting a load current. Further, if a second skin contact sensor is provided, it is possible to detect a lift of skin 13 by suction of a negative pressure. The detection may be displayed on display section 37.

In this way, if a negative pressure is created on skin 13 when skin 13 is punctured with laser light, skin 13 that become in a state of tension from relaxing, so that it is possible to collect blood 16 efficiently even if the prick by the puncturing is small. Therefore, the pain of the patient is alleviated. Further, by lifting skin 13 up to a predetermined position by a negative pressure and specifying the position, it is possible to focus the emitted laser light near the skin correctly.

Next, puncture button 75 is pressed (step 84). A signal of puncture button 75 is recognized by electrical circuit section 36. When electrical circuit section 36 starts up laser emitting apparatus 33, laser light is emitted toward skin 13. By setting the puncturing voltage of the laser light approximately 300 V, the pain the patient feels is alleviated.

Next, blood is collected (step 85). Blood 16 flowing out from skin 13 of the patient punctured with the laser light is stored in storing part 49 of blood sensor 42 (see FIG. 7, for example). Blood 16 stored in storing part 49 intrudes into supply channel 50 by capillary action and is led to detecting section 51. When blood 16 led to detecting section 51 reaches detection electrode 55 as the sensing electrode, detection electrode 55 determines that the amount of blood 16 required for measurement is obtained. At this time, negative pressure means 34 may be stopped, or negative pressure means 34 may be stopped after skin contact sensor 62 detects a non-contact of the skin.

When blood 16 flowing out from skin 13 is not guided into blood sensor 42 and remains on the skin, an absorbing means provided in tip part 41h of holder 41 in blood sensor unit 44 wipes off the blood (step 86). Step 86 may be performed after step 85 and may be performed after the measurement of glucose (step 87), the measurement of the Hct level (step 88) and the correction of the amount of the blood components (step 89).

On the other hand, when blood 16 is not detected by detecting section 51 after a predetermined time has passed or when the amount of blood 16 is not adequate (which is detected using the resistance between detection electrode 54 and detection electrode 55), a warning means maybe started for warning, and the detail of appropriate treatment may be displayed on display section 37.

Next, glucose is measured (step 87). After glucose in blood and glucose oxidation-reduction enzyme are reacted for a certain period, glucose maybe measured by applying a voltage between detection electrode 54 as the active electrode and detection electrode 56 as the counter electrode.

Further, the Hct level is measured (step 87). When a voltage is applied between detection electrode 57 as an active electrode and detection electrode 54 as a counter electrode, a current that depends on the Hct level is detected. The Hct level is measured based on this current.

Finally, the amount of the blood components is corrected (step 88). That is, using the Hct level measured in step 87, the glucose content calculated in step 86 is corrected. When measurement of the blood sugar level is finished through the above-described steps, blood sensor unit 44 after use is discarded.

A Schematic Flow of the Test Method

FIG. 34 schematically illustrates a flowchart of measuring steps in more detail. In FIG. 34, step 151 shows a state before blood sensor unit 44 is attached to adapter 40 of blood test apparatus 31. Step 152 shows a state where blood sensor unit 44 is inserted into adapter 40 along guide part 63 (see FIG. 31). Step 153 shows a state where connectors 61 are pressed and connectors 61 abut on contact parts 54b to 57b and 56c of sensor 42.

In the next step 154 a main switch of blood test apparatus 31 is turned on. Electrical circuit section 36 detects reference electrode 56d automatically out of electrodes, and specifies detection electrodes 54 to 57. Display section 37 then displays that preparation for measurement is completed.

In step 155, the end part of blood sensor unit 44 of blood test apparatus 31 is made to abut on skin 13. After step 155 in FIG. 34, apparatus body 39 of blood test apparatus 31 is omitted, and only blood sensor unit 44 is shown. Instep 156, blood test apparatus 31 is made to abut on skin 13 of the patient. First skin contact sensor 62 detects skin 13 when blood test apparatus 31 abuts on skin 13.

In step 157, when first skin contact sensor 62 detects skin 13, negative pressure means 34 starts operating and vacuums negative pressure chamber 60 as shown by arrow 157a. As a result of the vacuuming, skin 13 is lifted up.

When a negative pressure is created so as to further lift up skin 13 as shown in step 158, skin 13 abuts on second skin contact sensor (skin contact electrode) 110m. Second skin contact sensor 110m is set on the reverse side of blood sensor 42 attached on the lower face of blood sensor unit 44 (see FIG. 15), or set on the lower face of attaching part 120b (see FIG. 16) when blood sensor 42 is attached on the upper face of blood sensor unit 44. Second skin contact sensor 110m only has to detect a contact between skin 13 and blood sensor 42, and, for example, an optical sensor, a mechanical switch or an electrical resistance detection element may be used instead of an electrode.

In step 159, the suction of skin 13 into negative pressure chamber 60 is stopped. When second skin contact sensor 110m is not provided, the suction may be stopped after a predetermined time has passed from starting negative pressure means 34. The time passed may be measured with timer 79 of electrical circuit section 36.

In next step 160 skin 13 is irradiated with laser light and punctured. By this puncturing, blood 16 flows out from skin 13. Skin 13 may be punctured automatically when second skin contact sensor 110m detects skin 13. Alternatively, it is also possible to allow the patient to press puncture button 75 (see FIG. 32) based on an information on display section 37 that blood sensor unit 44 abuts on skin 13. In a case that the patient presses puncture button 75, the patient can get ready for puncturing.

As shown in step 161, blood 16 flowing out from skin 13 fills storing part 49 and flows into supply channel 50. Blood 16 flows into supply channel 50 by capillary action in supply channel 50 and suction from air hole 52 by negative pressure means 34. As shown in step 162, blood 16 is led to detecting section 51 of blood sensor 42. When the inflow of blood 16 to detecting section 51 is detected, the operation of negative pressure means 34 is stopped (step 163). When blood 16 reaches detection electrode 55 (see FIG. 8) of sensor 42, the inflow of blood 16 is detected. Then, vent switch 34c is operated, and the pressure in negative pressure chamber 60 is made equal to the outside atmospheric pressure.

Next, as shown in step 164, blood test apparatus 31 is released from skin 13. When measurement is finished, display section 37 displays that the measurement is finished. Then, the flow shifts to step 165, and display section 37 displays the result of measuring collected blood 16.

A Plurality of Times of Negative Pressure Creations

Figure 35:
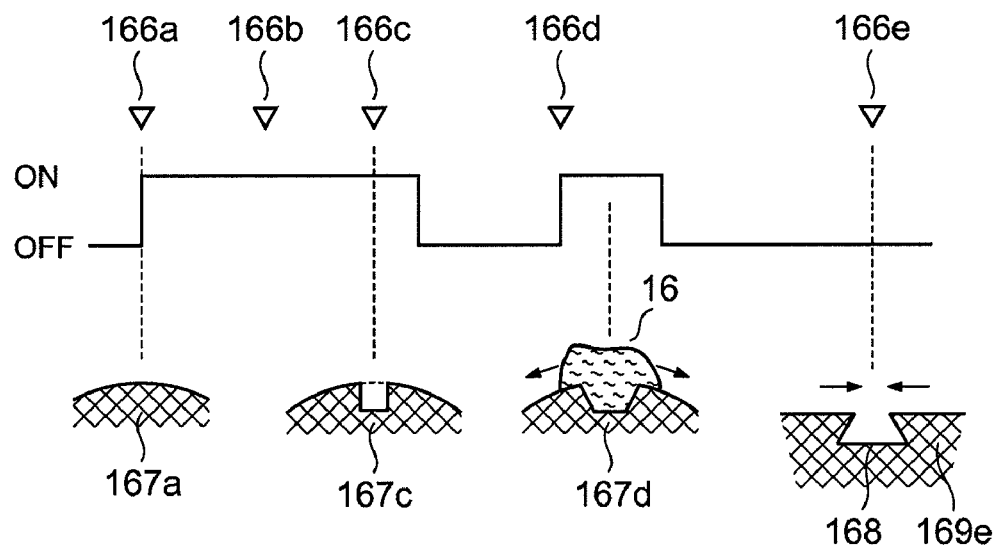
FIG. 35 shows a state where a negative pressure is created a plurality of times on an irregular basis in a blood test using the blood test apparatus.

The blood test apparatus of the present invention may create a negative pressure a plurality of times on an irregular basis after puncturing. The timing of creating a negative pressure and its operation will be described with reference to FIG. 35 and FIG. 36. When first skin contact sensor 62 detects skin 13, negative pressure means 34 starts being driven at time 166a (step 156 in FIG. 34). A negative pressure is created in negative pressure chamber 60, and skin 13 is placed in a state of tension and lifted as shown in state 167a (step 157 in FIG. 34). Skin 13 is lifted and abuts on second skin contact sensor 110m at time 166b (step 158 in FIG. 34). At time 166b, skin 13 is as shown in state 167b in FIG. 36. Here, a negative pressure supplied to negative pressure chamber 60 is stopped (step 159 in FIG. 34). Then, at time 166c, skin 13 is punctured (step 160 in FIG. 34). Skin 13 becomes as shown in state 167c, and blood 16 leaks.

Then, after supply of a negative pressure is once stopped, a negative pressure is created again at time 166d. By a negative pressure, the opening part of skin 13 widens as shown in state 167d, so that blood 16 flows out more easily (step 161 in FIG. 34). In this way, one of the reasons that a negative pressure is created on an irregular basis is to widen the hole punctured in skin 13 and collect blood 16 more easily. Another reason is to prevent blood 16 from gushing out and being oversampled when suction is performed by a burst of strong negative pressure. Therefore, negative pressure means 34 is operated on an irregular basis to such an extent that blood 16 does not overflow. In this way, power is saved by weakening the sucking force, and an adequate amount of blood 16 is collected. When an adequate amount of blood 16 is obtained and accurate measurement is finished, blood test apparatus 31 is removed from skin 13 (step 164 in FIG. 34). At time 166e when the measurement is finished, as shown in state 169e, wound 168 widened by a negative pressure, of skin 13, is sealed again. Therefore, the wound heals faster.

For some patients, little blood 16 flows out from skin 13 even if skin 13 is punctured with laser light. In such a case, it is also possible to make blood 16 flow out easily by increasing the negative pressure after puncturing compared to the negative pressure before puncturing. Given that the maximum pressure (negative pressure) is fixed, a negative pressure is controlled by controlling the period valve 34b is closed. Further, it is also possible to adopt a configuration where a negative pressure is created continuously without driving the negative pressure means on an irregular basis.

INDUSTRIAL APPLICABILITY

The blood test apparatus of the present invention makes replacement of a puncturing needle unnecessary or makes treatment after measurement simple, and so is suitable for use as blood test apparatuses in the field of medicine.

The disclosures of Japanese Patent Application No. 2006-078425, filed on Mar. 22, 2006, including the specification, drawings and abstract, is incorporated herein by reference in its entirety.

The invention claimed is:

1. A blood test apparatus comprising:
an apparatus body that has an opening part;
a blood sensor that is held at the opening part;
a puncturing section that is provided inside the apparatus body and that punctures skin;
an electrical circuit section that is connected to the blood sensor; and
a power supply section that supplies power to the electrical circuit section, wherein:
the blood sensor is included in a blood sensor unit that can be attached to and removed from the apparatus body, and forms therein a blood storing part which can sample a body fluid including blood to be tested; and
the blood sensor unit has a part that contacts the skin upon a blood test, and has an absorbing section for absorbing a body fluid including a part of blood from punctured skin punctured with the puncturing section, said blood part not being sampled with the blood storing part so as to remain on the punctured skin; and
the absorbing section including a blood absorbing member is set apart and distinct from the blood storing part, and is arranged closer to the part that contacts the skin upon the blood test than is the storing part.

2. The blood test apparatus according to claim 1, wherein the absorbing section contacts with the skin upon the test.

3. The blood test apparatus according to claim 1, wherein the absorbing section comprises a groove that produces capillary action.

4. The blood test apparatus according to claim 1, wherein the absorbing section comprises one or a plurality of grooves that are formed in a lower face, outer face or inner face of the blood sensor unit.

5. The blood test apparatus according to claim 1, wherein:
the lower face of the blood sensor unit is inclined with respect to a contacting skin surface; and an inner periphery of the lower face of the blood sensor unit projects toward the skin further than an outer periphery of the lower face of the blood sensor unit.

6. The blood test apparatus according to claim 1, wherein the absorbing section comprises one or a plurality of absorbent elastic members.

7. The blood test apparatus according to claim 6, wherein the elastic member is impregnated with an antiseptic.

8. The blood test apparatus according to claim 6, wherein the elastic member is placed in the lower face, outer face or inner face of the blood sensor unit.

9. The blood test apparatus according to claim 6, wherein the elastic member is embedded inside the lower face, outer face or inner face of the blood sensor unit.

10. The blood test apparatus according to claim 1, wherein the absorbing section comprises an accordion-shaped extensible member.

11. The blood test apparatus according to claim 10, wherein a seal member is placed in a tip of the accordion-shaped extensible material.

12. The blood test apparatus according to claim 1, wherein the absorbing section comprises an absorbent elastic member that is placed outside the blood sensor unit, and a through-hole that communicates between the elastic member and an interior of the blood sensor unit.

13. The blood test apparatus according to claim 12, wherein the absorbing section comprises a plurality of the through-holes.

14. The blood test apparatus according to claim 1, further comprising a negative pressure section that is provided inside the apparatus body,
wherein the negative pressure section can create a negative pressure inside the blood sensor unit.

15. The blood test apparatus according to claim 1, wherein:
the absorbing section comprises a groove that produces capillary action and communicates with an interior of the blood sensor unit; and
the blood test apparatus further comprises a negative pressure section that is provided inside the apparatus body and that can create a negative pressure inside the blood sensor unit.

16. The blood test apparatus according to claim 1, wherein the absorbing section comprises a groove that produces capillary action and one or a plurality of absorbent elastic bodies.

\* \* \* \* \*